US005792920A

United States Patent [19]
Bridges et al.

[11] Patent Number: 5,792,920
[45] Date of Patent: Aug. 11, 1998

[54] PLANTS WITH ALTERED ABILITY TO SYNTHESIZE STARCH AND PROCESS FOR OBTAINING THEM

[75] Inventors: Ian George Bridges, Silchester; Philip Anthony Fentem, Wokingham; Wolfgang Walter Schuch, Crowthorne, all of United Kingdom; Peter Lewis Keeling, Ames; George William Singletary, Ankeny, both of Iowa; Mark Olive, Cook, Australia

[73] Assignee: Imperial Chemical Industries PLC, London, England

[21] Appl. No.: 274,366

[22] Filed: Jul. 13, 1994

Related U.S. Application Data

[63] Continuation of Ser. No. 930,935, Aug. 18, 1992, abandoned, which is a continuation-in-part of Ser. No. 435,020, Nov. 13, 1989, abandoned.

[30] Foreign Application Priority Data

Nov. 10, 1988 [GB] United Kingdom ............... 8826356

[51] Int. Cl.$^6$ ............... A01H 5/00; C12N 15/29; C12N 15/54; C12N 15/82
[52] U.S. Cl. ............... 800/205; 435/101; 435/172.3; 435/194; 536/23.6; 800/DIG. 9; 800/DIG. 14; 800/DIG. 17; 800/DIG. 23; 800/DIG. 25; 800/DIG. 26; 800/DIG. 31; 800/DIG. 35; 800/DIG. 42; 800/DIG. 44; 800/DIG. 52; 800/DIG. 55; 800/DIG. 56; 800/DIG. 57; 800/DIG. 58; 800/DIG. 65; 800/DIG. 66; 800/DIG. 69
[58] Field of Search ............... 800/205, 250, 800/DIG. 9, DIG. 14, DIG. 17, DIG. 23, DIG. 25, DIG. 26, DIG. 31, DIG. 35, DIG. 42, DIG. 44, DIG. 52, DIG. 55, DIG. 56, DIG. 57, DIG. 58, DIG. 65, DIG. 66, DIG. 69; 435/172.3, 101, 194; 536/23.6, 23.2

[56] References Cited

U.S. PATENT DOCUMENTS 5,004,864  4/1991  Robertson et al. ............... 800/235

OTHER PUBLICATIONS

Napoli et al., (Apr. 1990) The Plant Cell 2:279, Abstract.
Van der Krol et al (Apr. 1990) The Plant Cell 2: 291, Abstract.
Smith et al (1990) Plant Molecular Biology 14: 369–379.
Tin et al (1988) Plant Physiol 86:1131–1135.
Krishnan et al (1986) Plant Physiol. 81 (2): 642–645.
Reeves et al (1986) Plant Physiol 82:34–40.
Morell et al (1987) Plant Physiol. 85:182–187.
Maniatis et al., Molecular Cloning. A Laboratory Manual, Cold Spring Harbor, 1982 pp. 324–325.
Sanger et al (Dec. 1987) Proc Natl Acad Sci, USA 74 (12):5463–5467.
Chemical Abstracts, vol. 113, No. 19, 5 Nov. 1990, Columbus, Ohio, US; abstract No. 169141.
Chemical Abstracts, vol. 105, No. 11, 1986, Columbus, Ohio, US; abstract No. 92298.
Chemical Abstracts, vol. 105, No. 21, 1986, Columbus, Ohio, US; abstract No. 187740.
Chemical Abstracts, vol. 72, No. 17, 1970, Columbus, Ohio, US; abstract No. 86509.
Baecker, P.A., et al., "Biosynthesis of bacterial glycogen. Primary structure of Escherichia coli ADP–glucose synthetase as deduced from the nucleotide sequence of the glgC gene"; Journal of Biological Chemistry, vol. 258, 1983, Baltimore, MD US, pp. 5084–5088.
Olive, M.R., et al. "Isolation and nucleotide sequences of cDNA clones encoding ADP–glucose encoding ADP–glucose pyrophosphorylase polypeptide from wheat leaf and endosperm"; Plant Molecular Biology, vol. 12, 1989, pp. 525–538.
Breuning, G., Eds., et al. "Tailoring Genes for Crop Improvement –An Agricutural Perspective"; 1987, pp. 133–152.

*Primary Examiner*—David T. Fox
*Assistant Examiner*—Amy J. Nelson
*Attorney, Agent, or Firm*—Cushman Darby & Cushman IP Group of Pillsbury Madison & Sutro LLP

[57] ABSTRACT

Plants, particularly cereal plants, which have altered ability to synthesise starch are produced by inserting into the genome of the plant a gene encoding an enzyme of the starch biosynthetic pathway such that capacity to produce starch is improved or reduced. The gene encoding the enzyme ADP-glucose pyrophosphorylase has been isolated from wheat leaf and wheat endosperm tissue. The enzyme is essential to the biosynthesis of starch in plants. Addition of extra copies of the gene to a plant by transformation enhances starch production, increasing the food value of the crop. Conversely, insertion of a gene encoding mRNA antisense to the mRNA encoded by the endogenous ADP-glucose pyrophosphorylase gene will reduce starch production. cDNA sequences are provided which may be used to identify homologous sequences in other tissue and in other plants. The ADP-glucose pyrophosphorylase gene promoter may be used in the genetic manipulation of plants to alter their starch-synthesising ability.

5 Claims, 10 Drawing Sheets

FIG. 3.

Table III.2 : A typical purification of ADP-glucose pyrophosphorylase from wheat endosperm using protocol 2.

| Purification steps | Volume (ml) | Protein (mg/ml) | Activity (nkat/ml) | Total activity (nkat) | Yield (%) | Specific activity (nkat/mg) | Purification (-fold) |
|---|---|---|---|---|---|---|---|
| 39,000 x g supernatant | 10.0 | 7.56 | 70.99 | 709.7 | 100 | 9.38 | 1.0 |
| phenyl-Sepharose | 11.0 | 1.427 | 38.70 | 425.8 | 59.9 | 27.12 | 2.8 |
| MonoQ HR 5/5 | 6.0 | 0.233 | 34.95 | 209.7 | 33.8 | 150.00 | 16.1 |
| MonoQ HR 5/5 | 6.0 | 0.083 | 26.88 | 161.3 | 22.7 | 323.85 | 34.5 |
| Superose 12 HR 10/30 | 1.0 | 0.070 | 48.40 | 48.4 | 6.8 | 691.42 | 73.7 |

FIG. 4.

A) WL : AGA.1

```
         G  V  L  I  L  S  G  D  H  L  Y  R  M  D  Y  M  D  F  V  Q  S  H  R  Q  R  D  A  G  I  S  I  C  C  L  P  I  D  G  S  R
GGGGTGCTGATTCTTTCTGGCGATCACCTCTACCGTATGGACTACATGGATTTTGTTCAGAGTCATCGGCAGAGACGCGGGATCAGCATCTGTTGCTTGCCTATTGATGGCAGCCGG
         10        20        30        40        50        60        70        80        90       100       110       120

A  S  D  F  G  L  M  K  I  D  D  T  G  R  V  I  S  F  S  E  K  P  R  G  A  D  L  K  E  M  E  E  A  E  K  K  P  Y  I  A
GCGTCTGATTTTGGTCTCATGAAGATAGACGACACAGGAAGAGTTATTTCATTTAGTGAAAAACCGAGAGGAGCTGATTTAAAGGAAATGGAGGAAGCAGAAAAGAAACCATACATAGCT
         130       140       150       160       170       180       190       200       210       220       230       240

S  M  G  V  Y  I  F  K  K  E  I  L  L  N  L  L  R  W  R  F  P  T  A  N  D  F  G  S  E  I  I  P  A  A  A  R  E  I  N  V
TCAATGGGAGTATACATATTCAAGAAAGAGATACTTCTAAATCTTTTGAGATGGCGTTTTCCTACTGCAAATGATTTTGGATCTGAAATAATTCCAGCTGCAGCAAGAGAGATTAATGTA
         250       260       270       280       290       300       310       320       330       340       350       360

K  A  Y  L  F  N  D  Y  W  E  D  I  G  T  I  K  S  F  F  E  A  N  L  A  L  A  E  Q  P  S  K  F  S  F  Y  D  A  S  K  P
AAGGCATATCTTTTCAATGATTACTGGGAAGATATTGGAACTATCAAATCCTTCTTCGAAGCAAATCTTGCCCTTGCTGAACAGCCTTCAAAGTTCAGCTTCTATGATGCTAGCAAACCG
         370       380       390       400       410       420       430       440       450       460       470       480

M  Y  T  S  R  R  N  L  P  P  S  H  I  S  G  S  K  I  T  D  S  I  I  S  H  G  C  F  L  D  K  C  R  V  E  H  S  V  V  G
ATGTACACATCGCGAAGAAACCTACCACCATCTATGATCAGCGGTAGTAAGATCACTGATTCGATCATTTCCCATGGATGTTTCTTGGATAAATGCAGGGTAGAGCACAGTGTCGTTGGA
         490       500       510       520       530       540       550       560       570       580       590       600

I  R  S  R  I  G  S  N  V  H  L  K  D  T  V  M  L  G  A  D  F  Y  E  T  D  M  E  R  G  D  Q  L  A  E  G  K  V  P  I  G
ATCCGTTCTCGAATAGGCTCCAACGTACACCTCAAGGATACGGTAATGCTCGGTGCTGATTTCTATGAAACTGACATGGAAAGAGGCGACCAGCTGGCCGAAGGAAAGGTTCCGATTGGG
         610       620       630       640       650       660       670       680       690       700       710       720

I  G  E  N  T  S  I  Q  N  C  I  I  D  K  N  A  R  I  G  K  N  V  T  I  A  N  A  E  G  V  Q  E  A  D  R  A  S  E  G  F
ATCGGGGAGAACACTTCGATTCAAAACTGCATCATTGACAAGAATGCGAGGATAGGGAAGAATGTGACCATTGCTAACGCCGAGGGTGTACAGGAAGCGGACAGGGCGTCAGAAGGCTTC
         730       740       750       760       770       780       790       800       810       820       830       840

H  I  R  S  G  I  T  V  V  L  K  N  S  V  I  A  D  G  L  V  I
CACATCCGGTCCGGTATCACGGTTGTGCTGAAGAACTCGGTGATTGCGGATGGATTAGTCATATGAGCTGAAAAAAGGCGGTTCTCCAGTCCAGCAAGAGAAATAAA
         850       860       870       880       890       900       910       920       930       940
```

FIG. 5.

B) WE : AGA.3

```
         E  L  V  Q  K  H  V  D  D  N  A  D  I  T  L  S  C  A  P  V  G  E  S  R  A  S  E  Y  G  L  V  K  F  D  S  S  G  R  V  V
CGGAGCTTGTGCAGAAACATGTGGATGACAATGCTGACATTACTTTATCATGTGCCCCTGTTGGAGAGAGCCGGGCATCTGAGTACGGGCTAGTGAAGTTCGACAGTTCAGGCCGTGTGG
         10         20         30         40         50         60         70         80         90        100        110        120

Q  F  S  E  K  P  K  G  D  D  L  E  A  M  K  V  D  T  S  F  L  N  F  A  I  D  D  P  A  K  Y  P  Y  I  A  S  H  G  V  Y
TCCAATTTTCTGAGAAGCCAAAGGGTGACGATCTGGAAGCGATGAAAGTGGACACCAGTTTTCTCAATTTCGCCATCGACGACCCTGCTAAATATCCATACATTGCTTCTATGGGAGTCT
        130        140        150        160        170        180        190        200        210        220        230        240

V  F  K  R  D  V  L  L  N  L  L  K  S  R  Y  A  E  L  H  D  F  G  S  E  I  L  P  R  A  L  H  D  H  N  V  Q  A  Y  V  F
ATGTCTTCAAAAGAGATGTTCTGCTCAACCTTCTAAAGTCAAGATACGCAGAACTACATGACTTTGGGTCTGAAATCCTCCCGAGAGCTCTGCATGACCACAATGTACAGGCTTATGTCT
        250        260        270        280        290        300        310        320        330        340        350        360

T  D  Y  H  E  D  I  G  T  I  R  S  F  F  D  A  N  M  S  L  C  E  Q  P  P  K  F  E  F  Y  D  P  K  T  P  F  F  T  S  P
TCACTGACTACTGGGAGGACATTGGAACAATCAGATCCTTCTTCGATGCGAACATGTCCCTCTGCGAGCAGCCCCCAAAGTTCGAGTTTTATGATCCCAAAACTCCCTTCTTCACCTCGC
        370        380        390        400        410        420        430        440        450        460        470        480

R  Y  L  P  P  T  K  S  D  K  C  R  I  K  E  A  I  I  L  H  G  C  F  L  R  E  C  K  I  E  H  S  I  I  G  V  P  S  R  L
CTCGATACTTGCCACCAACAAAGTCAGACAAGTGCAGGATCAAAGAAGCGATCATTCTGCACGGCTGCTTCTTGCGTGAATGCAAAATCGAGCACTCCATCATCGGCGTTCCTTCACGCC
        490        500        510        520        530        540        550        560        570        580        590        600

N  S  G  S  E  L  K  N  A  M  H  M  G  A  D  S  Y  E  T  E  D  E  I  S  R  L  M  S  E  G  K  V  P  I  G  V  G  E  N  T
TAAACTCCGGAAGCGAACTCAAGAACGCGATGATGATGGGTGCGGATTCGTACGAGACCGAGGATGAGATCTCGAGGCTGATGTCCGAGGGCAAGGTCCCCATCGGCGTCGGGGAGAACA
        610        620        630        640        650        660        670        680        690        700        710        720

K  I  S  N  C  I  I  D  M  N  A  R  I  G  R  D  V  V  I  S  N  K  E  G  V  Q  E  A  D  R  P  E  E  G  Y  Y  I  R  S  G
CAAAGATCAGCAACTGCATCATCGACATGAACGCGAGGATAGGAAGGGACGGTGGTCATCTCAAACAAGGAGGGAGTGCAAGAAGCCGACAGGCCGGAGGAGGGGTACTACATCAGGTCCG
        730        740        750        760        770        780        790        800        810        820        830        840

I  V  V  I  Q  K  N  A  T  I  K  D  G  T  V  V
GGATCGTGGTGATCCAGAAGAACGCGACCATCAAGGACGGCACCGTCGTGTAGTACCCGGGTCGGCGTGACGGGTTCTGCGACAACCTCTCGCTGCGTTGATCGTCGTCGTCGTCTCGAG
        850        860        870        880        890        900        910        920        930        940        950        960

GCCCGGGAGGGACTGAAGAAGTGACCGGGGACGGGAGGCGTTTGAAGCTTGAATGACTGAGAAGGCGCGCGCGGGCAGCATTAGTAGTAAGTAGTAGTAAGGAGCAGTGGAACAAAGTAA
        970        980        990       1000       1010       1020       1030       1040       1050       1060       1070       1080

TAGTCGTTCGTTTTTCCCCTGTAATAAATAAGAGGCTGTGTGTTGAGGTAAAGAAGTGGCAGCGAGCAAACAAACTCCCGGGGGATGTTCGTGTAAATAAAACTCTATCTAGACCTGTGA
       1090       1100       1110       1120       1130       1140       1150       1160       1170       1180       1190       1200

AATTTTCAAAAAAAAAAAAAAAAAAAAAAAAAAAAAAAAAAAAAAAAAAAAAAAAAAAAAA
       1210       1220       1230       1240       1250       1260       1270
```

FIG. 6.

C) WE: AGA.7

```
         R  A  S  P  P  S  E  S  R  A  P  L  R  A  P  Q  R  S  A  T  R  Q  H  Q  A  R  Q  G  P  R  R  M  C  N  G  G  R  G  P  P
CGTGCGTCTCCCCCGTCAGAGTCGAGGGCTCCGCTGCGAGCGCCTCAAAGGTCGGCGACACGGCAGCATCAGGCACGACAGGGTCCCAGGAGGATGTGCAACGGCGGCAGGGGCCCGCCA
         10       20       30       40       50       60       70       80       90      100      110      120

Y  H  T  A  G  V  T  S  A  P  A  R  Q  T  P  L  F  S  G  R  P  S  G  G  L  S  D  P  N  E  V  A  A  V  I  L  G  G  G  T
TACTGGACAGCTGGTGTCACCTCCGCCCCAGCCCGGCAGACACCCTTGTTCTCCGGACGTCCTTCAGGAGGATTAAGCGATCGAACGAGGTTGCGGCCGTCATACTCGGCGGCGGCACC
        130      140      150      160      170      180      190      200      210      220      230      240

G  T  Q  L  F  P  L  T  S  T  R  A  T  P  A  V  P  I  G  G  C  Y  R  L  I  D  I  P  M  S  N  C  F  N  S  G  I  N  K  I
GGGACTCAGCTCTTCCCACTCACGAGCACAAGGGCCACACCTGCTGTTCCTATTGGAGGATGTTACAGGCTCATCGACATTCCCATGAGCAACTGCTTCAACAGTGGCATCAACAAGATA
        250      260      270      280      290      300      310      320      330      340      350      360

F  V  M  T  Q  F  N  S  A  S  L  N  R  H  I  H  R  T  Y  L  G  G  G  I  N  F  T  D  G  S  V  E  V  L  A  A  T  Q  M  P
TTCGTCATGACCCAGTTCAACTCGGCCTCCCTTAATCGTCACATTCACCGCACCTACCTCGGCGGGGGAATCAATTTCACTGATGGATCCGTTGAGGTATTGGCCGCGACGCAAATGCCC
        370      380      390      400      410      420      430      440      450      460      470      480

G  E  A  A  G  W  F  R  G  T  A  D  A  H  R  K  I  I  H  V  L  E  D  Y  Y  K  N  K  S  I  E  H  I  L  I  L  S  G  D  Q
GGGGAGGCTGCTGGATGGTTCCGCGGAACAGCGGACGCGTGGAGAAAAATTATCTGGGTGCTTGAGGACTATTATAAGAATAAATCCATAGAGCACATTTTGATCTTGTCGGGCGATCAG
        490      500      510      520      530      540      550      560      570      580      590      600

L  Y  R  M  D  Y  M  E  L  V  Q  K  H  V  D  D  N  A  D  I  T  L  S  C  A  P  V  G  E  S  R  A  S  E  Y  G  L  V  K  F
CTTTATCGCATGGATTACATGGAGCTTGTGCAGAAACATGTGGATGACAATGCTGACATTACTTTATCATGTGCCCCTGTTGGAGAGAGCCGGGCATCTGAGTACGGGCTAGTGAAGTTC
        610      620      630      640      650      660      670      680      690      700      710      720

D  S  S  G  R  V  V  Q  F  S  E  Q  P  K  G  D  D  L  E  A  M  K  V  D  T  S  F  L  N  F  A  I  D  D  P  A  K  Y  P  Y
GACAGTTCAGGCCGTGTGGTCCAGTTTTCTGAGCAGCCAAAGGGTGACGATCTGGAAGCGATGAAAGTGGACACCAGTTTTCTCAATTTCGCCATCGACGATCCTGCTAAATATCCATAC
        730      740      750      760      770      780      790      800      810      820      830      840

I  A  S  M  G  V  Y  V  F  K  R  D  V  L  L  N  L  L  K  S  R  Y  A  E  L  H  D  F  G  S  E  I  L  P  R  A  L  H  D  H
ATTGCTTCTATGGGAGTCTATGTCTTCAAAAGAGATGTTCTGCTCAACCTTCTAAAGTCAAGATATGCAGAACTACATGACTTTGGGTCTGAGATCCTCCCGAGAGCTCTGCATGACCAC
        850      860      870      880      890      900      910      920      930      940      950      960

N  V  Q  A  Y  V  F  T  D  Y  H  E  D  I  G  T  I  R  S  F  F  D  A  N  R  A  L  C  E  Q  P  P  K  F  E  F  Y  D  P  K
AATGTACAGGCTTATGTCTTCACTGACTACTGGGAGGACATTGGAACAATCAGATCCTTCTTCGATGCAAACAGGGCCCTCTGCGAGCAGCCCCCAAAGTTCGAGTTTTATGATCCCAAA
        970      980      990     1000     1010     1020     1030     1040     1050     1060     1070     1080

T  P  F  F  T  S  P  R  Y  L  P  P  T  K  S  D  K  C  R  I  K  E  A  I  I  L  H  G  C  F  L  R  E  C  K  I  E  H  T  A
ACTCCCTTCTTCACCTCGCCTCGATACTTGCCACCAACAAAGTCAGACAAGTGCAGGATCAAAGAAGCGATCATTCTGCACGGCTGCTTCTTGCGTGAATGCAAAATCGAGCACACTGCG
       1090     1100     1110     1120     1130     1140     1150     1160     1170     1180     1190     1200

F  S  R  L  N  S  G  S  E  L  K  N  A  M  M  M  G  A  D  S  Y  E  T  E  D  E  M  S  R  L  M  S  E  G  K  V  P  I  G  V
TTCTCACGCCTAAACTCCGGAAGCGAGCTCAAGAATGCGATGATGATGGGCGCGGACTCGTACGAGACCGAAGCGAGATGTCGAGGCTGATGTCGGAGGGCAAGGTCCCCATCGGCGTC
       1210     1220     1230     1240     1250     1260     1270     1280     1290     1300     1310     1320

G  E  N  T  K  I  S  N  C  I  I  D  M  N  A  R  I  G  R  D  V  V  I  S  N  K  E  G  V  Q  E  A  D  R  P  E  E  G  Y  Y
GGGGAGAACACAAAGATCAGCAACTGCATCATCGACATGAACGCGAGGATAGGAAGGGACGTGGTCATCTCAAACAAGGAGGGAGTGCAAGAAGCCGACAGGCCGGAGGAGGGGTACTAC
       1330     1340     1350     1360     1370     1380     1390     1400     1410     1420     1430     1440

I  R  S  G  I  V  V  I  Q  K  N  A  T  I  K  D  G  T  V  V
ATCAGGTCCGGGATCGTGGTGATCCAGAAGAACGCGACCATCAAGGACGGCACCGTCGTGTAGTACCCGGGCCGGCGCGACGGGTTCCGCGACAACCTCTCTGCGCTGATCGTCGTCGT
       1450     1460     1470     1480     1490     1500     1510     1520     1530     1540     1550     1560

CGGCTTCTCGGGGCCGGGACTGGAGGAGTGACCGGGACGGGGGGCGTTTGAAGCTTTGAATGGCTGAGACTGAAAGTGGAGGCGCGCGCAGGCAGCATCAGTAGTAAGTAGTAAGTGGT
       1570     1580     1590     1600     1610     1620     1630     1640     1650     1660     1670     1680

AGTAAGTAGCAGTGGAACAAAGTAATAGTCGTTCGTTTTGCCCCTGTAATAAATAAGAAGGCTGTGTGTTGAGGTAAAGAAGTGGCCGCGAGCAAACAAAAAAAAAAAAAAAAAAA
       1690     1700     1710     1720     1730     1740     1750     1760     1770     1780     1790
```

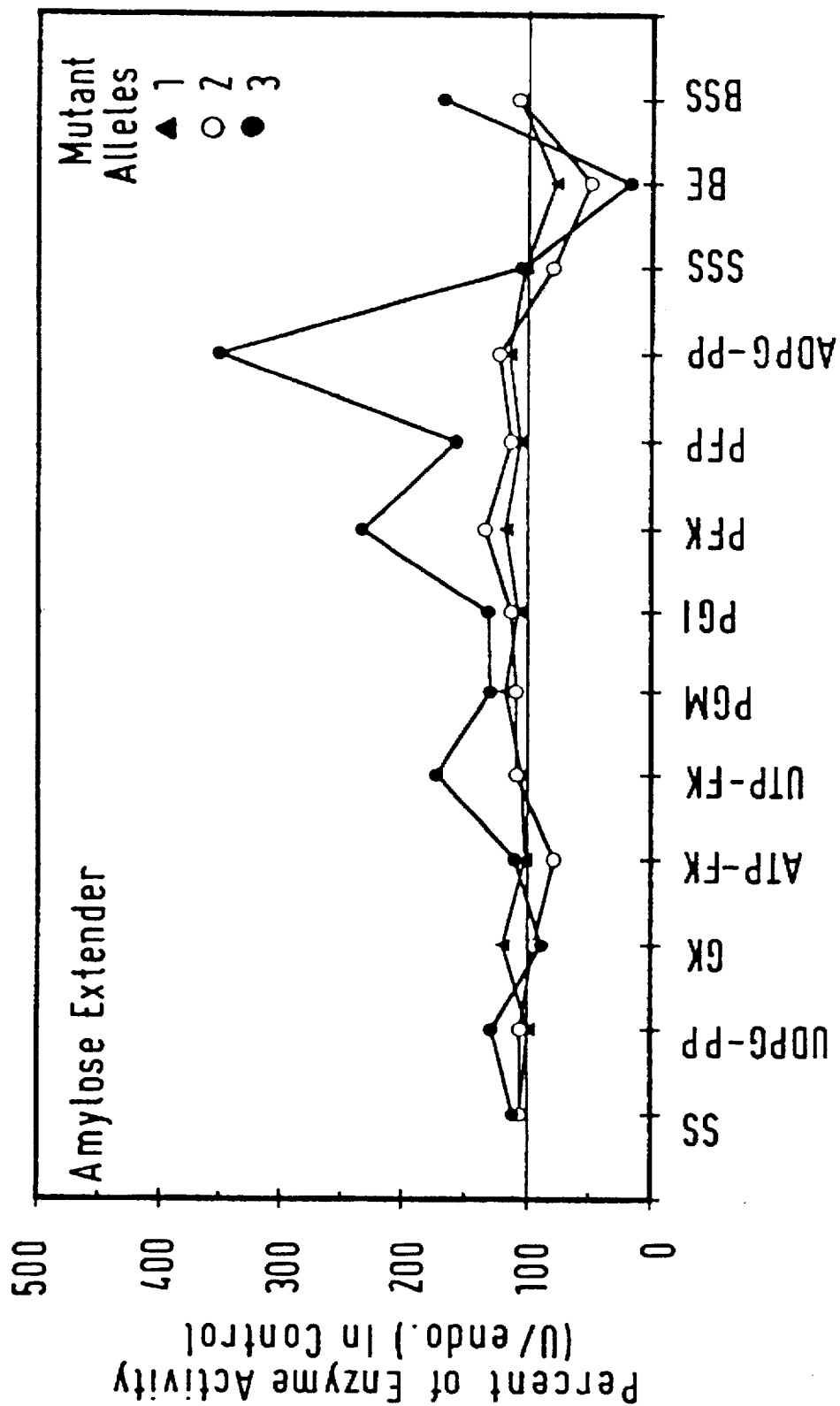

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  Ala  Ser  Ser  Met  Leu  Ser  Ser  Ala  Ala  Val  Ala  Thr  Arg  Thr  Asn
1                  5                            10                           15

Pro  Ala  Gln  Ala  Ser  Met  Val  Ala  Pro  Phe  Thr  Gly  Leu  Lys  Ser  Ala
                20                           25                      30

Ala  Phe  Pro  Val  Ser  Arg  Lys  Gln  Asn  Leu  Asp  Ile  Thr  Ser  Ile  Ala
               35                      40                      45

Ser  Asn  Gly  Gly  Arg  Val  Gln  Cys
          50                      55
```

( 2 ) INFORMATION FOR SEQ ID NO:2:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Ala  Pro  Thr  Val  Met  Met  Ala  Ser  Ser  Ala  Thr  Ala  Thr  Arg  Thr
1                  5                            10                           15

Asn  Pro  Ala  Gln  Ala  Ser  Ala  Val  Ala  Pro  Phe  Gln  Gly  Leu  Lys  Ser
                20                           25                      30

Thr  Ala  Ser  Leu  Pro  Val  Ala  Arg  Arg  Ser  Ser  Arg  Ser  Leu  Gly  Asn
               35                      40                      45

Val  Ala  Ser  Asn  Gly  Gly  Arg  Ile  Arg  Cys
          50                      55
```

( 2 ) INFORMATION FOR SEQ ID NO:3:

( i ) SEQUENCE CHARACTERISTICS:
        ( A ) LENGTH: 73 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:3:

```
Met Ala Ala Leu Ala Thr Ser Gln Leu Val Ala Thr Arg Ala Gly Leu
  1               5                  10                  15
Gly Val Pro Asp Ala Ser Thr Phe Arg Arg Gly Ala Ala Gln Gly Leu
             20                  25                  30
Arg Gly Ala Arg Ala Ser Ala Ala Ala Asp Thr Leu Ser Met Arg Thr
         35                  40                  45
Ala Ser Ala Arg Ala Ala Pro Arg His Gln Gln Gln Ala Arg Arg Gly
     50                  55                  60
Gly Arg Phe Pro Ser Leu Val Val Cys
 65                  70
```

(2) INFORMATION FOR SEQ ID NO:4:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Ala Gln Ile Leu Ala Pro Ser Thr Gln Trp Gln Met Arg Ile Thr
  1               5                  10                  15
Lys Thr Ser Pro Cys Ala Thr Pro Ile Thr Ser Lys Met Trp Ser Ser
             20                  25                  30
Leu Val Met Lys Gln Thr Lys Lys Val Ala His Ser Ala Lys Phe Arg
         35                  40                  45
Val Met Ala Val Asn Ser Glu Asn Gly Thr
     50                  55
```

(2) INFORMATION FOR SEQ ID NO:5:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Arg Ala Ser Pro Pro Ser Glu Ser Arg Ala Pro Leu Arg Ala Pro Gln
  1               5                  10                  15
Arg Ser Ala Thr Arg Gln His Gln Ala Arg Gln Gly Pro Arg Arg Met
             20                  25                  30
Cys
```

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ser Gly Ile Xaa Xaa Xaa Xaa Lys
 1           5
```

PLANTS WITH ALTERED ABILITY TO SYNTHESIZE STARCH AND PROCESS FOR OBTAINING THEM

This is a continuation of application Ser. No. 07/930,935, filed Aug. 18, 1992, now abandoned, which was abandoned upon the filing hereof which is a continuation-in-part of application Ser. No. 07/435,020 (abandoned) filed Nov. 13, 1989.

BACKGROUND OF THE INVENTION

This invention relates to novel plants, especially cereal plants, having an altered ability to produce starch, and to processes for obtaining such plants. This invention also relates to the isolation, purification and characterisation of the enzyme ADP-glucose pyrophosphorylase and the production of antibodies which can be used in the identification of ADP-glucose pyrophosphorylase cDNA clones. The invention further relates to the use of DNA clones to increase or decrease starch yield in cereals such as wheat, rice, maize and barley.

Starch is an important end-product of carbon fixation during photosynthesis in leaves and is an important storage product in seeds and fruits. In economic terms, the starch produced by the edible portions of three grain crops, wheat, rice and maize, provide approximately two-thirds of the world's food calculated as calories.

Starch is synthesized in the plastid compartment, the chloroplast, in photosynthetic cells or the amyloplast in non-photosynthetic cells. The biochemical pathway of starch biosynthesis in leaves has been well-characterised. FIG. 1 shows the reactions involved in the biosynthetic pathways of starch and glucose in leaves. The abbreviations used are: G-3-P,glyceraldehyde-3-phosphate; DHAP, dihydroxyacetone phosphate; $P_i$, orthophosphate; $PP_i$, inorganic pyrophosphate. The reactions are catalysed by the following enzymes:

1) phosphoglycerate kinase/glyceraldehyde-3-phosphate dehydrogenase
2) triose-phosphate isomerase
3) aldolase
4) fructose-1,6-bisphosphatase
5) hexose phosphate isomerase
6) phosphoglucomutase
7) ADP-glucose pyrophosphorylase
8) starch synthase
9) UDP-glucose pyrophosphorylase
10) sucrose phosphate synthase
11) sucrose phosphatase
12) orthophosphate/triose phosphate translocator
13) inorganic pyrophosphatase.

In contrast, little is known of the pathway of starch biosynthesis in storage organs. However, the recent development of a method for the isolation of intact amyloplasts from wheat endosperm cells has contributed to the elucidation of the pathway of starch biosynthesis in that organ. Our studies have led to a new understanding of the metabolic pathway of starch synthesis in developing starch storing tissues and of the factors controlling starch deposition in plants (Keeling et al, 1988, Plant Physiology, 87:311–319; Keeling, 1989: ed. C. D. Boyer, J. C. Shannon and R. C. Harrison, pp. 63–78, being a presentation at the 4th Annual Penn State Symposium in Plant Physiology; Olive et al, 1989, Plant Molecular Biology, 22:525–538). FIG. 2 shows the proposed metabolic pathway of starch biosynthesis in wheat endosperm (Keeling et al, 1988). The abbreviations used are the same as in FIG. 1. The reactions are catalysed by the following enzymes:

1) sucrose synthase
2) UDP-glucose pyrophosphorylase
3) hexokinase
4) phosphoglucomutase
5) hexose-phosphate isomerase
6) ATP-dependent phosphofructokinase
7) $PP_i$-dependent phosphofructokinase
8) aldolase
9) triose-phosphate isomerase
10) hexose-phosphate translocator (?)
11) ADP-glucose pyrophosphorylase
12) starch synthase
13) sucrose phosphate synthase
14) sucrose phosphatase.

We have established that grain filling rate and duration is governed by factors in the grain itself rather than being due to some component of the source tissues. Since starch comprises up to 75% of the grain dry weight in cereals it is logical that the limitation to plant dry matter accumulation will be most likely due to an effect on starch deposition. This suggests that cereal species or varieties with higher yield will be characterised by either longer duration of starch synthesis in the grain or greater rates of starch synthesis.

Research has shown that the pathways of starch biosynthesis in wheat leaves and wheat endosperm are different (FIGS. 1 and 2). Despite these differences in the overall pathway, the enzymic steps that facilitate the conversion of ADP-glucose to final starch assembly in both types of plastid are identical. Thus, in both cases the enzymes ADP-glucose pyrophosphorylase converts glucose-1 phosphate to ADP-glucose, whilst starch is synthesised from ADP-glucose through the combined actions of starch synthase and branching enzyme.

The plastid enzyme ADP-glucose pyrophosphorylase is an important regulatory enzyme of starch biosynthesis in photosynthetic plant organs. The activity of chloroplast ADP-glucose pyrophosphorylase is regulated post-translationally by the allosteric effectors 3-phosphoglycerate and orthophosphate. All plant leaf ADP-glucose pyrophosphorylase enzymes studied are activated in vitro by 3-phosphoglycerate, and to a lesser extent by fructose-1,6-bisphosphate, fructose-6-phosphate and phosphoenol pyruvate. These metabolites lower the Km values of substrates and increase the $v_{max}$ of the enzyme-catalysed reaction.

In addition, the ADP-glucose pyrophosphorylase enzymes from plant leaves are inhibited in vitro by orthophosphate, with half-maximal inhibition of enzyme activity generally achieved in orthophosphate concentrations of less than 100 µM.

Leaf starch biosynthesis is regulated in vivo by fluctuations in the chloroplastic levels of 3-phosphoglycerate and orthophosphate, at the level of the ADP-glucose pyrophosphorylase enzyme. Crucial to this regulatory mechanism is the selective permeability of the chloroplast inner membrane. It has been shown that the inner membrane of chloroplasts is selectively permeable to triose-phosphates, dicarboxylates and orthophosphate, which are rapidly and specifically transported from the chloroplast to the cytosol and vice versa. This active transport mechanism involves the counter-balancing inward movement of orthophosphate from the cytosol via the phosphate/triose-phosphate translocator. The active transport of metabolites via the orthophosphate/triose-phosphate translocator is involved in altering the ratio of orthophosphate to 3-phosphoglycerate (i.e. [Pi]/[3-PGA]) within the plastid during normal light-dark transitions. During photosynthesis, the 3-phosphoglycerate formed from $CO_2$-fixation accumulates in the chloroplast. The concentration gradient produced in 3-phosphoglycerate from the inside of the chloroplast to the cytosol leads to the export of some 3-phosphoglycerate into the cytosol in exchange for orthophosphate. The imported orthophosphate is subsequently utilised in ATP formation via photophosphorylation, so that the overall chloroplastic ratio of [Pi]/[3PGA] remains low during the light cycle. Thus, the ADP-glucose pyrophosphorylase enzyme is allosterically activated in the light, allowing starch biosynthesis to continue. During the dark cycle, there is decreased $CO_2$-fixation and decreased photophosphorylation, coupled with increased chloroplastic orthophosphate concentration as a result of the hydrolysis of ATP. This produces a high chloroplastic ratio of [Pi]/[3-PGA], thereby inhibiting ADP-glucose pyrophosphorylase activity and starch formation.

In addition to the modulation of ADP-glucose pyrophosphorylase activity by allosteric effectors, leaf starch biosynthesis is also probably regulated by the adenylate energy charge of the chloroplast.

The most important regulatory feature of starch biosynthesis in the developing endosperm is probably a coarse control mechanism via regulation of the synthesis of starch biosynthetic enzymes. There has been considerable emphasis in recent research on the identification of a rate-limiting enzyme in the starch biosynthetic pathway. Unfortunately, studies measuring the in vitro enzyme activities of starch biosynthetic enzymes throughout cereal endosperm development have not shed much light on this problem, since it is difficult to correlate in vitro and in vivo enzyme activities and most of the starch biosynthetic enzymes appear to be expressed co-ordinately.

At present there is no evidence that post-translational regulation of ADP-glucose pyrophosphorylase operates in vivo in cereal storage organs, although there is some evidence for in vitro allosteric regulation. For all cereal endosperm enzymes, the presence of 3-phosphoglycerate reduces the sensitivity of the enzyme to inhibition by orthophosphate, indicating that 3-phosphoglycerate binds to the enzyme, close to the site for binding of orthophosphate. The ADP-glucose pyrophosphorylase enzyme from maize endosperm is activated in vitro by 3-phosphoglycerate to a similar extent as the enzyme isolated from plant leaves. In contrast, the ADP-glucose pyrophosphorylase enzyme from rice endosperm is only activated 1.2-fold in vitro, by 5 mM 3-phosphoglycerate. Despite the conservation of sites for the binding of allosteric effectors in the endosperm ADP-glucose pyrophosphorylase enzymes, and the ability of the maize endosperm enzyme to be strongly activated in vitro by 3-phosphoglycerate, the in vivo significance of these allosteric effects is uncertain. The amyloplast pathway of starch synthesis is dissimilar to the pathway in chloroplasts as there is no direct involvement of triose phosphates. Hence allosteric regulation of ADP-glucose pyrophosphorylase appears to have a more minor in vivo role in cereal endosperm amyloplasts.

SUMMARY OF THE INVENTION

According to the prevent invention there is provided a method of producing a plant with altered starch synthesising ability comprising stably incorporating into the genome of a recipient plant one or more than one donor gene specifying an enzyme involved in the starch biosynthetic pathway such that the capacity of the plant to produce starch is improved or reduced.

The invention also provides plants having one or more than one donor gene stably incorporated into its genome such that its capacity to produce starch is improved or reduced. Such plants are capable of producing starch at a faster or slower rate and/or are capable of producing higher or lower starch yields. The invention also provides the seeds and progeny of such plants, and hybrids whose pedigree includes such plants.

The above method is generally applicable to all plants producing or storing starch. The recipient plant may be: a cereal such as maize (corn), wheat, rice, sorghum or barley; a fruit-producing species such as banana, apple, tomato or pear; a root crop such as cassava, potato, yam or turnip; an oilseed crop such as rapeseed, sunflower, oil palm, coconut, linseed or groundnut; a meal crop such as soya, bean or pea; or any other suitable species. Preferably the recipient plant is of the family Gramineae and most preferably of the species Zea mays.

The donor gene may be an additional copy of the gene specifying the normal enzyme present in the plant. The recipient plant is hence capable of producing higher starch yields.

In another embodiment, the donor gene may specify a modified allelic form of the enzyme with kinetic or allosteric properties different to those of the endogenous plant enzyme. For example, the enzyme encoded by the donor gene may have a greater activity or may show enhanced temperature-stability. Again, the recipient plant is capable of producing higher starch yields. Genes encoding improved allelic forms may be obtained from suitable biological organisms, or endogenous wild-type genes may be manipulated by standard protein or genetic engineering techniques.

Increased gene expression may also be elicited by introducing multiple copies of enhancer sequences into the 5'-untranscribed region of the donor gene.

In the alternative, the donor gene may be an anti-sense sequence which reduces expression of the enzyme in the recipient plant. Such a plant shows reduced starch deposition.

It is possible to insert more than one copy of the donor gene into the recipient genome. Each donor gene may be identical, or a combination of different donor genes may be incorporated. For example, the donor genes may have differing sequences which may encode more than one allelic form of the enzyme or may be derived from more than one source.

In one embodiment of the invention the said donor gene is derived from a sexually compatible donor plant and is inserted into the recipient plant by sexual crossing of donor and recipient plants.

In a second embodiment of the invention the donor gene is isolated from a suitable biological organism, which may be, for example, a bacterium, a fungus or a plant. Insertion of the donor gene is effected by genetic transformation of the recipient plant. If the donor organism is not sexually compatible with the recipient, the gene to be incorporated into the recipient plant genome is excised from the donor organism and the genome of the recipient plant is transformed therewith using known molecular techniques.

When altering a cereal's starch synthesising ability by the above or other methods of genetic manipulation, a variety of promoters may be used to drive the donor gene(s). However, it would be particularly advantageous to use a plant promoter which directs gene transcription to the endosperm as this is the site of major starch production. In addition, it would be advantageous to use a promoter which directs gene transcription in response to the physiological status of the cell. Thus starch synthesis in the cell would be more responsive to the specific environment and hence more efficient and/or more effective. Our study of the regulation of starch synthesis and in particular of ADP-glucose pyrophosphorylase enzyme expression has indicated that the ADP-glucose pyrophosphorylase gene promoter is endosperm-specific and particularly responsive to its environment.

The invention further provides a promoter sequence obtainable from a gene encoding the cereal enzyme ADP-glucose pyrophosphorylase. Such a promoter may be valuable as an endosperm-specific and responsive promoter for use in the genetic manipulation of crop plants to alter their starch synthesising ability.

Preferably the donor gene used in the above method specifies ADP-glucose pyrophosphorylase. As the enzyme seems to act as a control-point in starch biosynthesis, the rate of starch biosynthesis may be altered by manipulating the quantity or properties of this enzyme present in the plant. The ADP-glucose pyrophosphorylase gene may be obtained from various sources; for example it may be of plant origin or fungal origin or bacterial origin.

In practice, the above method may be used in maize to change the activities of ADP-glucose pyrophosphorylase enzyme in order to effect a change in flux of carbon through the starch synthesis pathway.

The invention further provides substantially pure ADP-glucose pyrophosphorylase.

The invention also provides a method for the purification of the enzyme ADP-glucose pyrophosphorylase, comprising subjecting a crude extract containing the enzyme to successive purification by gel chromatography. The crude enzyme may be isolated from wheat endosperm.

The invention also provides antibodies to the enzyme ADP-glucose pyrophosphorylase. Antibodies to the protein may be produced and used to screen cDNA expression libraries for the identification of ADP-glucose pyrophosphorylase cDNA clones.

Further, the invention provides DNA encoding ADP-glucose pyrophosphorylase, and plasmids containing said DNA. The DNA may be a cDNA sequence or a genomic DNA sequence. In particular, the invention provides:

(i) wheat leaf cDNA encoding ADP-glucose pyrophosphorylase and having he nucleotide sequence shown in FIG. 4, plasmid WL:AGA.1 containing same, and *E. coli* TG2 harbouring the plasmid (deposited at the National Collection of Industrial & Marine Bacteria on 19th Oct. 1988: Accession No. NCIB 40065;

(ii) wheat endosperm cDNA encoding ADP-glucose pyrophosphorylase and having the sequence shown in FIG. 5, plasmid WE:AGA.3 containing same, and *E coli* TG2 harbouring the plasmid (deposited at the National Collection of Industrial & Marine Bacteria on 19th Oct. 1988: Accession No. NCIB 40066; and, (iii) wheat endosperm cDNA encoding ADP-glucose pyrophosphorylase and having the nucleotide sequence shown in FIG. 6, plasmid WE:AGA.7 containing same, and *E coli* TG2 harbouring the plasmid (deposited at the National Collection of Industrial & Marine Bacteria on 19th Oct. 1988: Accession No. NCIB 40067.

These clones may be used as probes for equivalent genes in other organisms including plant species and in particular cereals such as wheat, maize, barley and sorghum and food crops such as potatoes. The probes may be used to screen cDNA libraries or genomic DNA libraries. In particular, the clones may be used as probes to isolate a genomic DNA clone containing a promoter sequence from the ADP-glucose pyrophosphorylase gene.

Additionally, the invention produces the enzymes expressed by the cDNAs (i), (ii) and (iii) above which have the amino acid sequences shown in FIGS. 4, 5 and 6 respectively.

The principal utility of the cDNAs defined is in the transformation of crop plants to regulate starch biosynthesis and, accordingly, the invention also provides transformed plants containing one or more copies of one or more of the cDNAs (i), (ii) and (iii) defined above.

In general, the invention provides a plant having improved capacity to produce starch and having stably incorporated within its genome one or more than one gene specifying ADP-glucose pyrophosphorylase.

The invention also provides a plant having reduced capacity to produce starch and having stably incorporated within its genome a gene specifying a mRNA antisense to the mRNA encoded by the ADP-glucose pyrophosphorylase gene.

The invention further provides the seeds and progeny of such plants, and hybrids derived from such plants.

The description which follows describes a method for the isolation of ADP-glucose pyrophosphorylase from wheat, the kinetic properties of the wheat endosperm and leaf enzymes, and methods for the isolation of cDNA clones encoding ADP-glucose pyrophosphorylase. The structural features of these cDNA clones are also described. These clones can be used for the isolation of the corresponding genes.

The cDNAs and the genes are used to alter starch yield in plants by the method described. The donor gene may be an additional copy of the gene specifying the normal ADP-glucose pyrophosphorylase enzyme present in the plant. The recipient plant is hence capable of producing higher starch yields.

One possible application is the use of these DNA sequences to increase gene dosage of ADP-glucose pyrophosphorylase in transformed crop plants to determine the contribution of ADP-glucose pyrophosphorylase to the net regulation of starch biosynthesis. The introduction of one or more additional copies of a ADP-glucose pyrophosphorylase gene increases expression of the enzyme in endosperm amyloplasts, and will increase the levels of starch accumulated during, for example, grain filling in cereals.

In another embodiment, the donor gene may specify a modified allelic form of ADP-glucose pyrophosphorylase with kinetic or allosteric properties different to those of the endogenous plant enzyme. For example, the enzyme encoded by the donor gene may have a greater activity or may show enhanced temperature-stability. The latter property may enhance the duration of grain filling. Again, the recipient plant is capable of producing higher starch yields.

Starch-producing and glycogen-producing organisms (including plants, fungi and bacteria) may be used as sources of improved enzyme genes. Such organisms may be screened for allelic forms of the ADP-glucose pyrophosphorylase enzymes which are more catalytically active than those typically found in cereal food crops. The genes encoding such enzymes may be transferred into cereals and other crop plants by sexual crossing or by genetic engineering techniques. In addition, screening for enzymes showing a more temperature-stable duration of grain filling may be enhanced by RPLP-aided selection during the plant breeding and development process.

It is also possible to alter the kinetic properties of the enzyme in the recipient plant through protein and genetic engineering; for example, by the selection of enzymes less sensitive to orthophosphate inhibition, or by the manipulation of the orthophosphate binding site to make the enzymes less sensitive to orthophosphate inhibition. Genes encoding variants of ADP-glucose pyrophosphorylase with different kinetic or allosteric properties may be created using molecular techniques or mutagensis. For example, the sequence of the enzyme gene and/or its promoter and/or the transit peptide can be altered in order to achieve a more temperature-stable enzyme expression late in endosperm development. This is the time period when the duration of grain filling is normally being curtailed as a result of reduced activities of ADP-glucose pyrophosphorylase and other enzymes in the amyloplast compartment.

A number of parameters may be improved by protein and genetic engineering or biochemical selection of the enzyme. The DNA sequence encoding the improved protein may then be transformed into the genome of the recipient plant in order to change the regulation of starch deposition.

Increased gene expression may also be elicited by introducing multiple copies of enhancer sequences into the 5'-untranscribed region of ADP-glucose pyrophosphorylase gene.

In the alternative, the donor gene may be an anti-sense sequence which reduces expression of the ADP-glucose pyrophosphorylase enzyme in the recipient plant. Such a plant has reduced starch deposition.

It is possible to insert more than one copy of the donor gene into the recipient genome. Each donor gene may be identical, or a combination of different donor genes may be incorporated. For example, the donor genes may have differing sequences which may encode more than one allelic form of ADP-glucose pyrophosphorylase or may be derived from more than one source.

When incorporating an ADP-glucose pyrophosphorylase donor gene into a recipient plant, the construct will require the presence of an amyloplast transit peptide to ensure its correct localisation in the amyloplast. The transit peptide attached to ADPG pyrophosphorylase may itself be used (Plant Mol Biol Reporter, 1991, 9:104-126), and it is believed that chloroplast transit peptides have similar sequences. Other potential transit peptides are those of small subunit RUBISCO, acetolactate synthase, glyceraldehyde-3P-dehydrogenase and nitrite reductase. For example, the consensus sequence of the transit peptide of small subunit RUBISCO from many genotypes has the sequence:(SEQ. ID NO:1)

MASSMLSSAAV--ATRTNPAQAS MVAPFTGLKSAAPPVSRK QNLDTTTSIA SNGGRVQC;

the corn small subunit RUBISCO has the sequence: (SEQ ID NO:2)

MAPTVMMASSAT-ATRTNPAQAS AVAPPQGLKSTASLPVARR SSRSLGNVA SNGGRIRC;

the transit peptide of leaf starch synthase from corn has the sequence:(SEQ ID NO:3)

MA ALATSQLVAT RAGLGVPDAS TFRRGAAQGL RGA-RASAAAD TLSMRTASARA APRHQQQARR GGR-PPSLVVC;

the transit peptide of leaf glylceraldehyde-3P-dehydrogenase from corn has the sequence: (SEQ ID NO:4)

MAQILAPS TQWQMRITKT SPCATPITSK MWSSLVMKQT KKVAHSAKFR VMAVNSENGT;

the putative transit peptide from ADPG pyrophosphorylase from wheat has the sequence: SEQ ID NO:5

RASPPSESRA PLRAPQRSAT RQHQARQGPR RMC.

It is possible to express the ADP-glucose pyrophosphorylase constitutively using one of the well-known constitutive promoters such as CaMV35S but there may be biochemical penalties in the plant resulting from changed starch deposition throughout the entire plant. Deposition, in the endosperm is much preferred, and possible promoters include the ADPG pyrophosphorylase gene promoter, the starch synthase gene promoter, and the sucrose synthase gene promoter.

In summary, the following are examples of genetic manipulation methods which may be used to produce plants with an altered ability to synthesise starch:

(1) Insertion of an additional copy of the wild-type ADP-glucose pyrophosphorylase gene;
(2) Insertion of a more active enzyme gene which may be obtained from a biological organism;
(3) Insertion of multiple copies of the wild-type or enhanced activity enzyme gene;
(4) Modification of the ADP-glucose pyrophosphorylase gene by techniques known in protein engineering to achieve alterations in the kinetics and/or allosterics of the enzyme reaction;
(5) Modification of the promoter sequences using techniques known in protein engineering to achieve enzyme over-expression;
(6) Modification of the sequence of the enzyme gene and/or its promoter and/or the transit peptide.

The present invention will now be described, by way of illustration, by the following examples.

BRIEF DESCRIPTION OF THE DRAWINGS

FIG. 3 is a Table of data relating to the purification of ADP-glucose pyrophosphorylase.

FIG. 4 shows the DNA sequence of clone WL.AGA.1.

FIG. 5 shows the DNA sequence of clone WE.AGA.3.

FIG. 6 shows the DNA sequence of clone WE.AGA.7.

FIG. 7 shows the activity of starch synthetic enzymes in amylose extender maize.

DETAILED DESCRIPTION OF THE INVENTION

Figure 1:
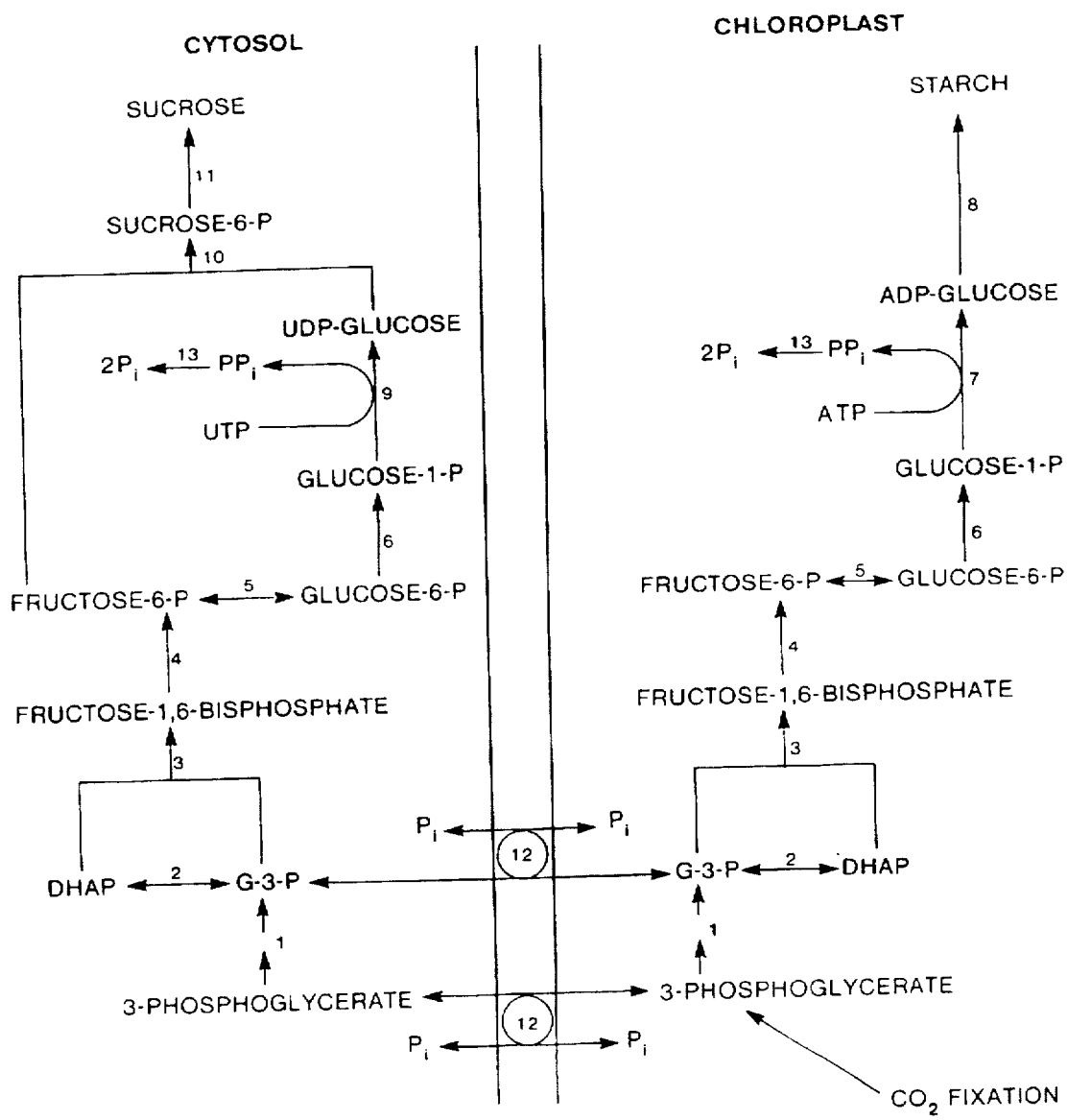
FIG. 1 shows the reactions involved in the biosynthetic pathways of starch and glucose in leaves.
Figure 2:
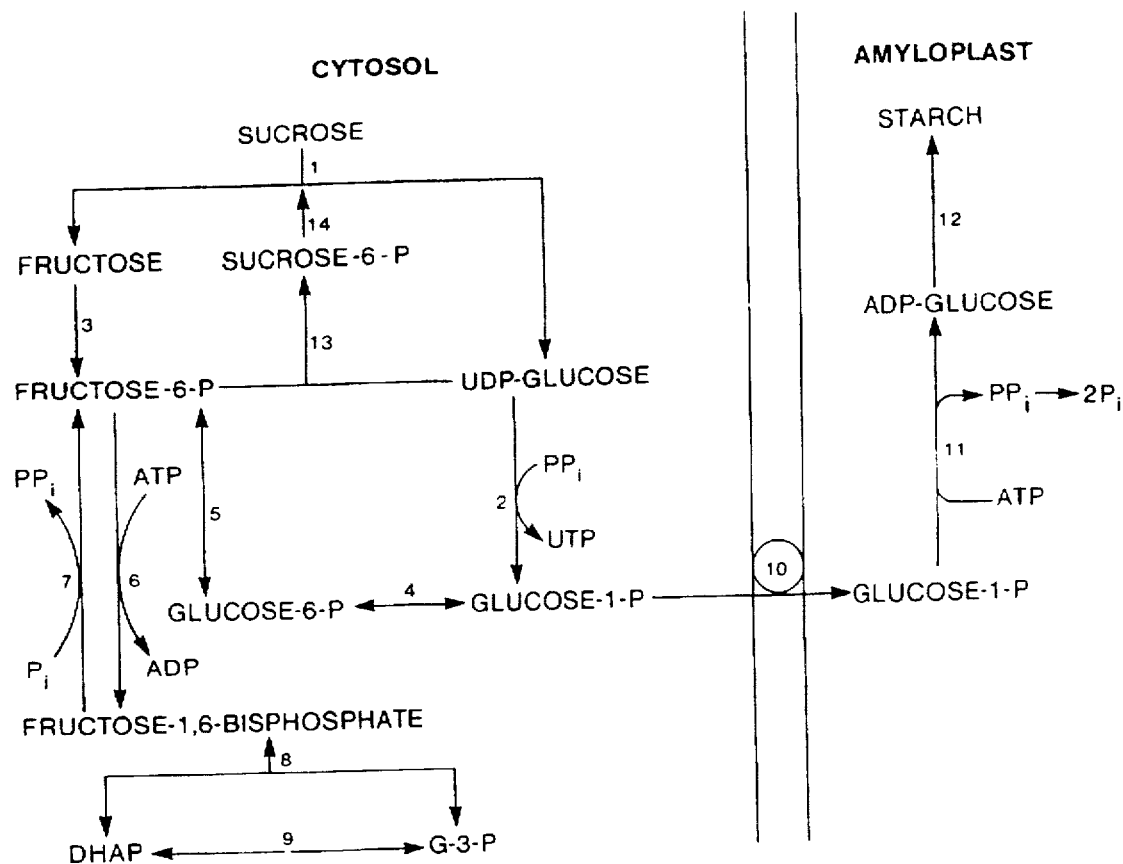
FIG. 2 shows the proposed metabolic pathway of starch biosynthesis in wheat endosperm.

1. Identification and Purification of Wheat Endosperm ADP-glucose Pyrophosphorylase 1.1 Purification of the Enzyme ADP-glucose pyrophosphorylase was partially purified by chromatography on phenyl-Sepharose, followed by two cycles of purification on the ion-exchange medium MonoQ HR 5/5 and one cycle of puriication through the gel filtration medium, Superose 12 HR 1-/30. Typical puriication results are presented in FIG. 3. Pooled ADP-glucose pyrophosphorylase extracts at each stage of the puriication procedure were analysed on an SDS/polyacrylamide gel. Following gel filtration there were very few protein contaminants in the enzyme preparation, which appeared to be greater than 90% pure. A polypeptide of 51,000 molecular weight was selectively purified at each stage of the purification. Thus, the wheat endosperm ADP-glucose pyrophosphorylase enzyme has a subunit molecular weight of 51,000.

The native molecular weight of wheat endosperm ADP-glucose pyrophosphorylase was determined to be 245,000±30,000, by re-chromatogrpahy of the partially purified enzyme on Superose 12 HR 10/30. This is consistent with the estimated molecular weight of 260,000±20,000, determined by chromatography of the protein on Sephacryl S-300 sf. In each case, the molecular weight was determined by comparison of the elution volume of ADP-glucose pyrophosphorylase activity with the elution volume of known protein standards, ferritin, catalase and bovine serum albumin. Thus, we conclude, the wheat endosperm enzyme consists of four subunits of identical molecular weight.

1.2 Kinetic Properties of the Enzyme

Partially-purified wheat endosperm ADP-glucose pyrophosphorylase is not activated by concentrations of up to 20 mM 3-phosphoglycerate. In contrast, the wheat leaf enzyme is activated 14.5-fold by 100 µM 3-phosphoglycerate. The wheat endosperm enzyme was found to be inhibited by orthophosphate, with 700 µM orthophosphate required to achieve half-maximal inhibition of enzyme activity. This is much more than the concentration required to achieve half-maximal inhibition of wheat leaf ADP-glucose pyrophosphorylase (56 µM). A similar lack of allosteric responsiveness of maize endosperm ADP-glucose pyrophosphorylase has been observed previously, although this phenomenon has since been attributed to the effect of protease activity on the enzyme during its extraction from the grain. Thus it has been demonstrated that maize endosperm ADP-glucose pyrophosphorylase is activated in vitro by 3-phosphoglycerate, when purified in the presence of 1.5 mM phenyl methane sulfonyl fluoride and 10 µg/ml chymostatin. However, we have purified the wheat endosperm ADP-glucose pyrophosphorylase enzyme in the presence of the protease inhibitors chymostatin, leupepetin and phenyl methone sulfonyl fluoride. We have been unable to demonstrate allosteric activation of this enzyme preparation in vitro by 3-phosphoglycerate. Thus, the results suggest that the wheat endosperm enzyme is not allosterically activated by 3-phosphoglycerate.

In contrast the wheat leaf ADP-glucose pyrophosphorylase was found to be activated by 3-phosphoglycerate, 1 mM giving 10-fold activation. Consistent with the antagonistic effects of 3 -phosphoglycerate and orthophosphate on plant leaf ADP-glucose pyrophosphorylase enzymes, inhibition of the wheat endosperm enzyme is relieved by 3-phosphoglycerate. In the presence of 1 mM 3-phosphoglycerate, the $I_{0.5}$ value of wheat endosperm ADP-glucose pyrophosphorylase for orthophosphate is increased to 1.5 mM. In the presence of 1 mM phosphate, 1 mM 3-phosphoglycerate gives 3-fold activation by reversing phosphate inhibition of the enzyme. Fructose-6-phosphate also weakly alleviates phosphate inhibition. 3-phosphoglycerate may activate wheat endosperm ADP-glucose pyrophosphorylase in vivo by alleviating phosphate inhibition. In view of this interaction of 3-phosphoglycerate and orthophosphate, the binding site for 3-phosphoglycerate is possibly close to the site for orthophosphate binding in the 3-dimensional structure of the enzyme.

The finding that the wheat endosperm enzyme has different allosteric properties from the maize endosperm enzyme suggests that there exists some significant variation in living organisms for this biochemical trait. Thus not only may there be some variant alleles in plants, but also there may be variants in other organisms that differ substantially in the kinetics of their interactions with the allosteric effectors. This hypothesis is strengthened by studies of enzyme allosteric properties in *E coli* where enzyme types were identified which lack allosteric properties.

1.3 Studies of Analogues of 3-Phosphoglycerate on Allosteric Properties

There is clear evidence that the wheat endosperm enzyme has allosteric properties by virtue of being inhibited by phosphate and the inhibition being partially relieved by 3-phosphoglycerate. This suggests the possibility that this inhibition could be effectively relieved by chemical analogues of 3-phosphoglycerate. A careful analysis of various chemical that were chemically very closely related to 3-phosphoglycerate was carried out.

Seventeen compounds were tested at 3 mM concentration for their ability to antagonise the inhibition of the enzyme by 1 mM phosphate. The first series of compounds tested were phosphonate analogues of 3-phosphoglycerate. Of these, one compound (phosphonomethyl-butanedioic acid) gave weak antagonism of phosphate inhibition. The second series tested were derivatives bearing structural similarity to 3-phosphoglycerate. Of these, only one compound gave weak alleviation of phosphate inhibition. Sulphate (3 mM) also antagonised phosphate inhibition.

This preliminary screen identified chemicals which only weakly mimicked 3-phosophglycerate in alleviating phosphate inhibition. It was concluded that the techniques of genetic engineering, aimed at introducing an ADP-glucose pyrophosphorylase enzyme less sensitive or insensitive to phosphate inhibition, would provide a more effective means of achieving higher activities of ADP-glucose pyrophosphorylase in vivo.

Variants of ADP-glucose pyrophosphorylase with different kinetic and allosteric properties may be purified from natural sources or created using molecular techniques or mutagenesis. Some forms of the enzyme may not be substantially different from the normal wild-type enzyme but favour starch deposition through a higher enzyme activity.

To isolate or produce genes encoding such enzymes it was first necessary to clone the wild-type gene(s) and determine its DNA sequence.

1.4 Generation of Antibodies To The Enzyme

Sufficient protein to enable the immunisation of rabbits was obtained by pooling the isolated enzyme subunit isolated as described above from a number of separate experiments. The 51 kD ADP-glucose pyrophosphorylase polypeptide was subsequently purified to apparent homogeneity by electroelution from polyacrylamide gel slices. Antisera were prepared against the 51 kD ADP-glucose pyrophosphorylase polypeptide. The immunisation of rabbits was carried out essentially according to Mayer and Walker (1978).

The immune sera obtained precipitated ADP-glucose pyrophosphorylase activity from crude extracts of wheat endosperm. Following incubation of extracts with immune serum and centrifugation of the enzyme-Igγ-protein A-Sepharose conjugates, only 10% of the ADP-glucose pyrophosphorylase activity remained in the supernatant fraction. The ADP-glucose pyrophosphorylase activity was detectable in the pellet fractions when the washed enzyme-Igγ-protein A-Sepharose conjugates were assayed directly for enzyme activity. Approximately 70% of the total enzyme activity present in the endosperm extracts was subsequently recovered as an immunoprecipitate in pellet fractions. In control experiments, pre-immune sera collected from animals prior to their primary immunisation with ADP-glucose pyrophosphorylase did not partition ADP-glucose pyrophosphorylase activity. Western blot analysis of total wheat endosperm soluble protein using anti-wheat endosperm ADP-glucose pyrophosphorylase serum revealed the presence of a single 51 kD immunoreactive polypeptide. In a similar experiment, antibodies directed against the spinach leaf ADP-glucose pyrophosphorylase holoenzyme also recognized one polypeptide only in wheat endosperm of 51 kD molecular weight.

1.5 Subunit Structure of Endosperm and Leaf Enzymes

The presence of organ-specific isoenzymes of ADP-glucose pyrophosphorylase in wheat leaf and wheat endosperm was confirmed by western blot analysis of protein extracts from these organs, using anti-wheat endosperm ADP-glucose pyrophosphorylase serum to detect the enzyme subunits. As mentioned previously, the wheat endosperm enzyme consists of four 51 kD subunits. In western blotting experiments to determine the subunit structure of the wheat leaf isoenzyme, there was no detectable immunoreactive protein band in the crude extracts of wheat leaves. Following chromatography of wheat leaf extracts on phenyl-Sepharose and Superose 12 HR 10/30, a single immunoreactive polypeptide with a molecular weight of 48.5–49.0 kD was detected in western blots. The wheat leaf ADP-glucose pyrophosphorylase polypeptide is therefore approximately 2.5 kD smaller than the corresponding protein from wheat endosperm. Further evidence for the difference between the leaf and the endosperm enzymes is presented below.

2. Isolation and Characterisation of Wheat ADP-glucose pyrophosphorylase cDNAs

2.1 Identification of a Wheat Leaf ADP-glucose Pyrophosphorylase cDNA Clone In order to identify a cDNA clone encoding wheat leaf ADP-glucose pyrophosphorylase, $3 \times 10^4$ bacteriophage from the amplified wheat leaf cDNA library were screened with anti-spinach leaf ADP-glucose pyrophosphorylase serum. Of seven positive clones selected on the first screening, three clones producing the strongest signals were re-screened. Only one of these clones produced strong positive signals in subsequent rounds of screening. The intensity of the signal produced by this cDNA clone, relative to non-recombinant λgt11 suggests that the clone contains a cDNA encoding wheat leaf ADP-glucose pyrophosphorylase. The putative wheat leaf ADP-glucose pyrophosphorylase cDNA clone was designated WL:AGA.1. DNA was prepared from clone WL:AGA.1. Following restriction endonuclease digestion of the DNA with the enzyme EcoR1 and agaorse gel electroporesis, clone WL:AGA.1 was shown to contain a cDNA insert of 950 bp in size. The cDNA insert was labelled with $^{32}$P by nick-transmission and used to probe a northern blot of poly(A)-containing RNA from wheat leaf and wheat endosperm. This probe hybridises to mRNA bands of approximately 1.8 kb and 1.7 kb in size, respectively, in the endosperm and leaf RNA samples. The sizes of the wheat leaf and wheat endosperm ADP-glucose pyrophosphorylase mRNAs determined here are in close agreement with the estimates obtained by Krishnan et al (1986), from northern blots of wheat RNAs probed with a cDNA encoding rice endosperm ADP-glucose pyrophosphorylase. Comparison of the size of the cDNA insert with the size of the homologous mRNA species, indicates that the WL:AGA.1 cDNA insert contains approximately 55% of the complete wheat leaf ADP-glucose pyrophosphorylase mRNA sequence.

2.2 Sequence Analysis of WL:AGA.1

The cDNA insert from clone WL:AGA.1 is 947 bp in length and encodes 301 amino acids at the C-terminus of wheat leaf ADP-glucose pyrophosphorylase (FIG. 4). Approximately 70% of the mature wheat leaf ADP-glucose pyrophosphorylase polypeptide sequence is contained in the WL:AGA.1 protein. The cDNA extends 45 nucleotides into the 3'-untranslated region of the corresponding mRNA and terminates at the putative polyadenylation signal AATAA, located at positions 942–947. Consequently, there is no poly(A) tail in the wheat leaf ADP-glucose pyrophosphorylase cDNA sequence. The hydropathy index (Kytee and Doolittle, 1982) and secondary structure predictions (Chou and Fasman, 1978) were calculated for the WL:AGA.1 protein using the programmes of Devereux et al (1987). The Kyte and Doolittle (1982) hydropathy index of the WL:AGA.1 protein is consistent with its location in the soluble fraction of chloroplasts (Kaiser and Bassham. 1979b). The secondary structure predictions of Chou and Fasman (1978) have been used in comparisons of the wheat leaf and wheat endosperm ADP-glucose pyrophosphorylase proteins (see below).

2.3 Isolation of Wheat Endosperm ADP-glucose Pyrophosphorylase cDNA Clones

A wheat endosperm cDNA library was constructed. Double-stranded cDNA was prepared from oligo dT-cellulose-purified wheat endosperm RNA by a method employing RNaseH and *E. coli* DNA polylmeraseI in the synthesis of the second strand, without prior purification of single-standard cDNA (Gubler and Hoffman, 1983). The unamplified wheat endosperm cDNA library was screened for the presence sequences homologous to the wheat leaf ADP-glucose pyrophosphorylase cDNA insert, WL:AGA.1. In a screen of $3 \times 10^4$ recombinant bacteriophage, 10 positive signals were detected. Six of these clones were plaque-purified during two additional rounds of screening and designated WE:AGA.1, WE:AGA.3, WE:AGA.4, WE:AGA.5, WE:AGA.6 and WE:AGA.7. DNA was prepared from these six putative wheat endosperm ADP-glucose pyrophosphorylase cDNA clones. Following restriction endonuclease digestion of the DNAs with EcoR1 and agarose gel electrophoresis, the sizes of the cDNA inserts of these clones were shown to range from 400 bp to 1800 bp.

2.4 Sequence Analysis of WE:AGA.3

The cDNA insert from clone WE:AGA.3 is 1272 bp in length (FIG. 5), which includes a poly(A) tail 65 nucleotides long, at the 3'-terminus. The 3-untranslated region of WE:AGA.3 cDNA, from the TAG stop codon to the start of the poly(A) tail, is 317 bp in length. There are two overlapping polyadenylation signals present in the 317 bp 3'untranslated region of WE:AGA.3 cDNA; the sequence AATAAA is located 104 bp upstream of the polyadenylation site, while the sequence AATAAG is 100 bp upstream of the polyadenylation site. Clone WE:AGA.3 also contains a third putative polyadenylation signal. AATAAA at position 1176–1181, 31 bp upstream form the polyadenylation site. Since the location of polyadenylation signals in plant mRNAs is usually 22–36 nucleotides upstream of the polyadenylation site (Joshi, 1987), then this third poly- adenylation signal in clone WE:AGA.3 is the signal most likely to be involved with selection of the poly(A) addition site during processing of the corresponding ADP-glucose pyrophosphorylase mRNA. The open reading frame of clone WE:AGA.3 is 890 bp is length, encoding 296 amino acids of wheat endosperm ADP-glucose pyrophosphorylase. Thus, a protein of 33,200 molecular weight is encoded by clone WE:AGA.3, which corresponds to 65% of the size of mature wheat endosperm ADP-glucose pyrophosphorylase subunits.

2.5 Sequence Analysis of WE:AGA.7

The largest wheat endosperm ADP-glucose pyrophosphorylase cDNA, WE:AGA.7 is 1798 bp in length (FIG. 6), comprising an open reading frame of 1500 bp. This open reading frame codes for a protein of 55,500 molecular weight, which exceeds the estimated molecular weight of the mature wheat endosperm ADP-glucose pyrophosphorylase polypeptide by approximately 4.5 kD. The amino acid sequence of the first 33 residues encoded by clone WE:AGA.7 exhibits properties similar to the transit peptides of chloroplast proteins (Colman and Robinson 1986) and to the transit peptide of the amyloplast protein, granule-bound starch synthase (Klosgen et al, 1986). The sequence is rich in hydroxylated and basic amino acids, especially arginine which occurs every 4–5 residues in the sequence. Despite the similarity in amino acid content of the putative ADP-glucose pyrophosphorylase transit peptide and the granule-bound starch synthase transit peptide, there is no obvious sequence homology. There is also no sequence homology to the transit peptide sequences of nuclear-encoded chloroplast proteins, for example the small subunit of Rubisco (Masur and Chui, 1985) and the 16 kD polypeptide of the oxygen-evolving complex (Jansen et al, 1987). The exact processing site for the pre-ADP-glucose pyrophosphorylase polpeptide has not been determined in these studies and will require N-terminal amino acid sequence analysis of the mature protein from wheat endosperm. However, cleavage of the precursor polypeptide between Met and Cys would produce a protein of 51,800, the approximate molecular weight of the mature ADP-glucose pyrophosphorylase. Furthermore, the chloroplast-specific transit peptide of the small subunit of Rubisco is also removed at the boundary between a cysteine and a methionine residue (Mazur and Chui, 1985), while the amyloplast-specific starch synthase transit peptide is removed at the boundary between a cysteine and an alanine residue (Klosgen et al, 1986).

In addition, clone WE:AGA.7 contains a 278 bp 3'-untranslated region, from the TAG stop codon to the start of the poly(A) tail. The untranslated region contains two overlapping putative polyadenylation signals, AATAAA at position 1728–1733 and AATAAG at position 1732–1737. These polyadenylation signals are located 45 bp and 41 bp respectively, from the polyadenylation site and are the same sequences present in clone WE:AGA.3. It is not possible at present to determine which of these signals may be functional. The Kyte and Doolittle (1982) hydropathy index and the Chou and Fasman (1978) secondary structure predictions were calculated for the WE:AGA.7 using the programme of Devereaux et al (1987). The Kyte and Doolittle (1982) hydropathy profile indicates that the WE:AGA.7 protein contains hydrophobic and hydrophobic domains interspersed throughout its length, consistent with it being a soluble protein.

3. Comparison of ADP-glucose Pyrophosphorylase Sequences 3.1 Comparison of WG:AGA.3 and WG:AGA.7

The wheat endosperm ADP-glucose pyrophosphorylase cDNA inserts of clones WE:AGA.3 and WE:AGA.7 are 96.3% homologous in the shared regions of their open reading frames. In the 3'-untranslated region of these clones, from the TAG stop codons to the polyadenylation site, the extent of homology is reduced to 72.3%. A detailed comparison of the nucleotide sequences of WE:AGA.3 and WE:AGA.7 cDNAs reveals a total of 30 base substitutions, of which 72% are transitions. Within the open reading frame there are only 18 base substitutions, 11 transitions and 7 transversions. It is noteworthy that all of the transitions are located in third base positions of codons and none of them leads to an amino acid substitution. One of the transversions, located at position 1296 in WE:AGA.7 is silent. The remaining six transversions produce three conservative (threonine-serine, glutamine-lysine, alanine-serine) and two semiconservative (argine-methionine, isoleucine-methionine) amino acid substitutions. In addition, there are only 9 insertions/deletions in the open reading frame, occurring at positions 579–585 and positions 592–593 of the WE:AGA.3 nucleotide sequence. These insertions/deletions produce an additional 5 amino acid changes between WE:AGA.3 and WE:AGA.7 proteins, three insertions and 2 substitutions. Thus, the derived amino acid sequences of the wheat endosperm ADP-glucose pyrophosphorylase cDNAs differ in only 10 of 296 amino acid residues, yielding an amino acid homology of 96.7%. In the 3'-untranslated region there are a total of 85 insertions/deletions between WE:AGA.3 and WE:AGA.7 sequences, clustered into 8 variable regions.

3.2 Comparison of WE.AGA.7 and WL.AGA.1

The wheat leaf ADP-glucose pyrophosphorylase cDNA sequence (WL:AGA.1) and the wheat endosperm ADP-glucose pyrophosphorylase cDNA sequence (WE:AGA.7) were compared using the DIAGON programme of Devereux et al (1987). There are 10 well-conserved domains between the two nucleotide sequences. Between WL:AGA.1 and WE:AGA.7, there are 322 nucleotide substitutions, 290 of which are within the open reading frame, plus 148 insertions/deletions. Thus, within the open reading frames for which the WL:AGA.1 and WE:AGA.7 cDNA sequences overlap, there is only 55.7% homology at the DNA level. There is no homology in the 3'-untranslated region represented in the clones.

To determine the homology between WE:AGA.7 and WL:AGA.1 encoded polypeptides, the derived amino acid sequences were aligned. Of the 290 nucleotides substitutions within the open reading frame, 97 are silent. There are a total of 110 amino acid alterations between the wheat leaf and wheat endosperm ADP-glucose pyrophosphorylase polypeptide sequences, produced by the remaining 193 nucleotide substitutions and 91 of the 148 insertions/deletions. This data indicates that, in most cases nucleotide substitutions between WL:AGA.1 and WE:AGA.7 cDNA sequences involve all three nucleotide positions of codons. Thus, there is only 55.3% homology between the derived amino acid sequences of these cDNAs.

Of the 110 amino acid substitutions between wheat leaf and wheat endosperm ADP-glucose pyrophosphorylase polypeptide sequences, 62 are conservative changes involving either no charge difference or substitution of charged residues for neutral amides (i.e. glutamine, asparagine), substitution of amphipathic residues for other amphipathic residues, or substitution of hydrophobic residues for other hydrophobic residues. There are 39 semi-conservative amino acid substitutions, involving reversal of charge, or substitution of amphipathic amino acids for charged, neutral, or hydrophobic residues. Non-conservative amino acid substitutions, of which there are 9, involve substitution of hydrophobic residues for either charged or neutral amino acids. Two of the non-conservative amino acid substitutions (His$_{512}$–Tyr$_{512}$; Lys$_{521}$–Gln$_{521}$) and two semi-conservative substitutions (Ser$_{508}$–Glu$_{508}$); Ala$_{527}$–Lys$_{527}$) between wheat leaf and wheat endosperm ADP-glucose pyrophosphorylase polypeptides are located in close proximity to, or within the region homologous to the putative 3-phosphoglycerate binding site on spinach leaf ADP-glucose pyrophosphorylase (Preiss et al, 1988). However, within the C-terminal 27 residues of wheat leaf and wheat endosperm ADP-glucose pyrophosphorylase enzymes the Chou and Fasman (1978) predictions are nearly identical.

3.3 Comparison of Clones by Restriction Mapping

Restriction maps of the wheat leaf and wheat endosperm ADP-glucose pyrophosphorylase cDNAs were constructed to demonstrate their relatedness. The restriction map of the wheat leaf ADP-glucose pyrophosphorylase cDNA is very different from the maps of wheat endosperm ADP-glucose pyrophosphorylase cDNAs, with no internal restriction enzyme sites in common. This result confirms previous hybridisation analysis, which indicates that the wheat leaf and wheat endosperm ADP-glucose pyrophosphorylase genes cDNAs represent separate gene sub-families. In contrast, the wheat endosperm cDNAs WE:AGA.1, WE:AGA.3, WE:AGA.5, WE:AGA.6 and WE:AGA.7 are closely related. The cDNAs all contain the unique HindIII site located at the 3'-terminus, and the SstI site located at position ~680 relative to the HindIII site. A unique BamHI site is present in the 5'-region of the longer cDNA inserts, WE:AGA.1, WE:AGA.6 and WE:AGA.7. There is polymorphism around the SstI site located at position ~400 relative to the HindIII site of the wheat endosperm ADP-glucose pyrophosphorylase cDNAs, since this site is present only in clones WE:AGA.1, WE:AGA.6 and WE:AGA.7. In addition, the BglII site located at position ~340 relative to the HindIII site, is only present in clones WE:AGA.3 and WE:AGA.5. These results suggest that the wheat endosperm ADP-glucose pyrophosphorylase gene sub-family may be divided into at least two distinct gene classes, with Class I represented by clones WE:AGA.3, WE:AGA.5 and Class II represented by clones WE:AGA.1, WE:AGA.6 and WE:AGA.7.

3.4 Comparison to Other ADP-glucose Pyrophosphorylase Polypeptides

The amino acid sequences derived from the wheat ADP-glucose pyrophosphorylase cDNAs were aligned with the amino acid sequences derived from a rice endosperm ADP-glucose pyrophosphorylase cDNA (Preiss et al, 1987) and the E. coli glgC gene (Baecker et al, 1983). The 5-way protein sequence alignment have been carried out.

The homologies between amino acid sequences were subsequently calculated on the basis of this alignment as the proportion of identical residues in the overlapping regions and do not therefore take into account the size of gaps between the overlaps. There is 40% homology between the wheat endosperm ADP-glucose pyrophosphorylase sequences (WE:AGA3 and WE:AGA.7) and rice endosperm ADP-glucose pyrophosphorylase. The wheat leaf sequence is 44% homologous to rice endosperm ADP-glucose pyrophosphorylase. These homologies are only slightly less than the 55% homology between wheat leaf and wheat endosperm sequences. In addition, there is 29.5% homology between the rice endosperm and E. coli amino acid sequences, compared to only 24% homology between the wheat leaf of wheat endosperm ADP-glucose pyrophosphorylase and E. coli ADP-glucose pyrophosphorylase.

3.5 Functional Protein Domains of ADP-glucose Pyrophosphorylase

Regions of the E. coli and spinach leaf ADP-glucose pyrophosphorylase polypeptide sequences have been identified previously as substrate, activator or inhibitor binding sites (Parsons and Preiss, 1978a, 1978b; Larsen et al, 1986; Lee and Preiss, 1986; J. Preiss, personal communications). The derived amino acid sequences of wheat leaf and wheat endosperm ADP-glucose pyrophosphorylase have been compared with substrate, activator and inhibitor binding sites identified on other ADP-glucose pyrophosphorylase enzymes. These binding sites form five protein domains.

3.5.1 The Fructose-1,6-bisphosphate Binding Site

The allosteric activator (fructose-1,6-bisphosphate) binding site of E. coli ADP-glucose pyrophosphorylase is located near the N-terminus of the protein close to the Lys$_{90}$ residue (Parsons and Preiss, 1978b). The amino acid sequence in wheat endosperm ADP-glucose pyrophosphorylase homologous to the fructose-1,6-bisphosphate binding site of the E. coli enzyme (Parsons and Preiss, 1978b) has been identified. The region from reside 78–100 has 14 out of the 23 amino acids conserved between what endosperm and E. coli sequences. However, there are major alterations at several amino acid positions, involving the substitution of charged residues in the E. coli sequence for hydrophobic or amphipathic residues in the wheat endosperm sequence, for example Arg$_{80}$–Thr$_{80}$, Lys$_{85}$–Phe$_{85}$, Asp$_{86}$–Pro$_{86}$, Lys$_{90}$–Thr$_{90}$, Lys$_{93}$–Thr$_{93}$, His$_{97}$–Pro$_{97}$. Since pyridoxal-5'-phosphate binds at Lys90 in E. coli ADP-glucose pyrophosphorylase, and fructose-1,6-bisphosphate binds in this region also (Parsons and Preiss, 1978a, 1978b), this binding site is probably not functional in the wheat endosperm protein. Thus, in the wheat endosperm sequence homologous to the allosteric site of E. coli ADP-glucose pyrophosphorylase, there is no opportunity for Schiff base formation between fructose-1,6-bisphosphate and the protein domain. This finding is consistent with the lack of detectable activation of wheat endosperm ADP-glucose pyrophosphorylase by fructose-1,6-bisphosphate. Unfortunately, the wheat leaf ADP-glucose pyrophosphorylase cDNA sequence does not extend far enough into the 5'-coding region to contain sequences of the fructose-1,6-bisphosphate binding site. We cannot be certain, therefore, whether allosteric activation of leaf ADP-glucose pyrophosphorylase by fructose-1,6-bisphosphate is achieved by binding of the activators to the same site as in the E. coli enzyme.

3.5.2 Substrate Binding Sites

Two substrate binding sites of the E. coli ADP-glucose pyrophosphorylase are well-conserved in the wheat leaf and wheat endosperm ADP-glucose pyrophosphorylase sequences. The region between residues 166–173 contains a consensus sequence of WXXGTADA, obtained from a comparison of wheat endosperm, rise endosperm and *E. coli* protein sequences in this region. In all cases amino acid position 167 is occupied by an aromatic hydrophobic residue, either tyrosine or phenylalanine. Comparison of ADP-glucose pyrophosphorylases reveals a consensus sequence of FXEXP for residues 252–256. In addition, binding of pyridoxal-5'-phosphate to $Lys_{255}$ of the *E. coli* ADP-glucose pyrophosphorylase is prevented by ADP-glucose indicating that the substrate binding site is nearby. Although pyridoxal-5'-phosphate forms a Schiffs base with e-amino group of lysine, it is unlikely that $Lys_{255}$ is itself involved in substrate binding since it is not strictly conserved in the plant ADP-glucose pyrophosphorylase sequences: Clone WE:AGA.7, for example encodes a glutamine residue at position 255. However. $Phe_{251}$ is strictly conserved in all of the ADP-glucose pyrophosphorylase sequences examined, indicating that this residue might be involved in binding ATP and ADP-glucose, by hydrophobic interaction between the planar aromatic ring of the phenylanine side-chain and the adenine ring of the substrate molecules. Nevertheless, an alternative mechanism involving ionic interaction between the phosphate moiety of ATP or ADP-glucose and the amino group of $Arg_{257}$ (or $Lys_{257}$) cannot be ruled out.

In the putative substrate binding domains of ADP-glucose pyrophosphorylase enzymes there is no amino acid homology with the consensus sequence of Higgins et al (1986) for ATP binding sites. That consensus sequence (GXXXXGKS) has been shown by crystallographic analysis to form the phosphate binding region (Pai et al, 1979, cited in Higgins et al, 1986). A variant of this sequence. GDQLAEGKV in the wheat leaf sequence and SRLMSEGKV in the wheat endosperm sequences is located at position 460–468.

3.5.3. The 3-phosphoglycerate Binding Site

Amino acid sequences were compared to amino acid sequence of the putative 3-phosphoglycerate binding site on spinach leaf ADP-glucose pyrophosphorylase. This site is highly conserved between wheat leaf and wheat endosperm sequences. Different activation kinetics of the wheat leaf and wheat endosperm ADP-glucose pyrophosphorylase enzymes are not explained in terms of altered binding sites for 3-phosphoglycerate, since there is no obvious correlation between enzyme activation and conservation of the 3-phosphoglycerate binding site. In addition, although the primary sequences of wheat endosperm and wheat leaf ADP-glucose pyrophosphorylases differ in 6 of the 13 residues of the 3-phosphoglycerate binding site, the secondary structure predictions for this sequence are nearly identical.

Since 3-phosphoglycerate is able to prevent the inhibition of the wheat endosperm ADP-glucose pyrophosphorylase by orthophosphate this suggests that the enzyme possesses a functional 3-phosphoglycerate binding site. A consensus sequence for the binding of 3-phosphoglycerate, between residues 515–522 is SGIXXXXK (SEQ ID NO:6) obtained by a comparison of all available plant ADP-glucose pyrophosphorylase sequences. Residue $Lys_{522}$ is strictly conserved in all sequences, and is involved with binding of pyridoxal-5'-phosphate, and probably also 3-phosphoglycerate, as found in the spinach leaf ADP-glucose pyrophosphorylase enzyme.

Thus, it is likely that alterations between wheat leaf and wheat endosperm ADP-glucose pyrophosphorylase amino acid sequences in regions other than the putative 3-phosphoglycerate binding site, are responsible for the observed differences in allosteric properties of these enzymes. Since the amino acid sequences of these two enzymes are only 55% homologous, any of the observed amino acid alterations might explain their different allosteric properties. This would suggest that the wheat endosperm enzyme might not be able to undergo the necessary conformational changes required to convert it to a more active form, in the presence of 3-phosophglycerate.

Figure 8:
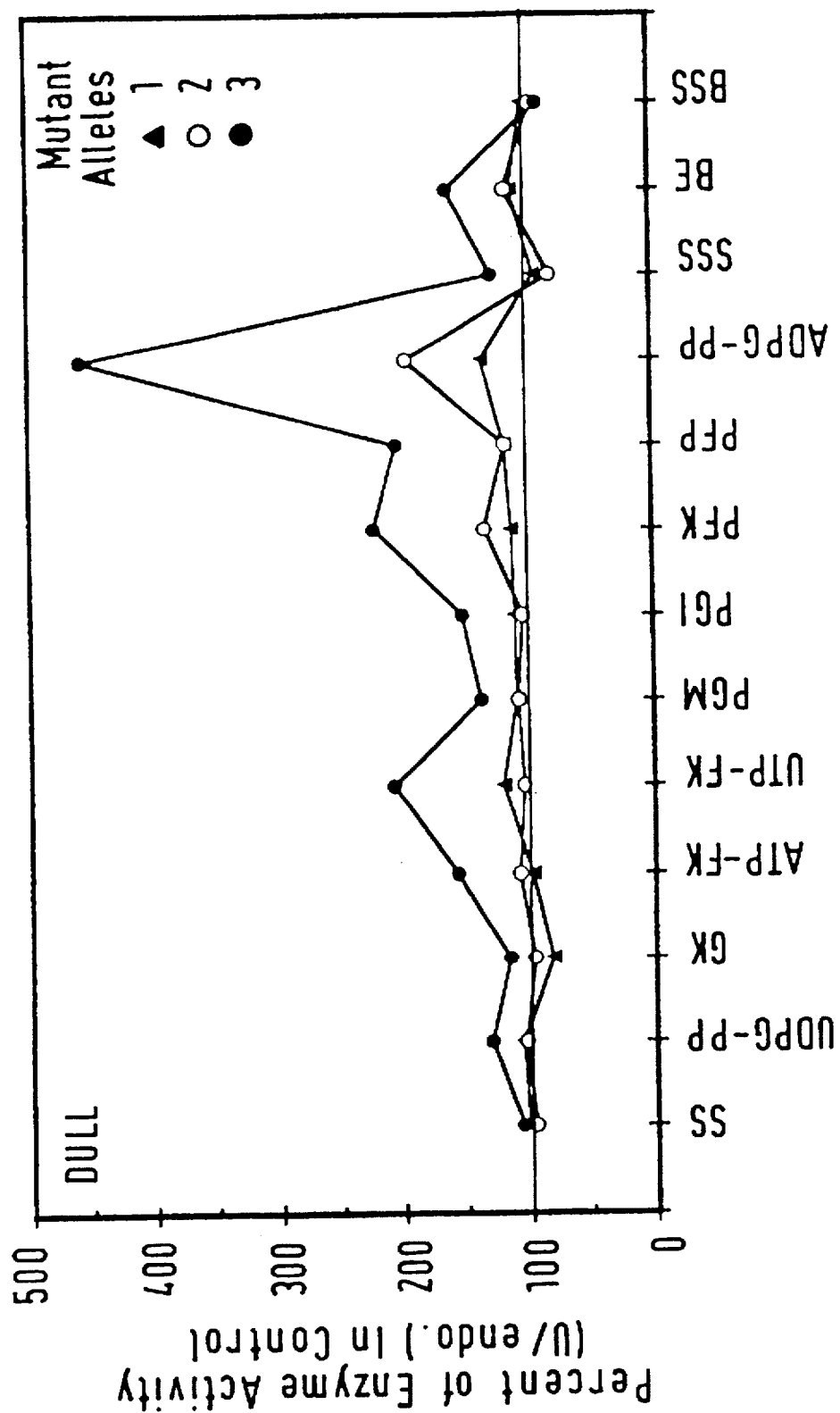
FIG. 8 shows the activity of starch synthetic enzymes in dull maize.

4. Studies of ADP-glucose Pyrophosphorylase Activities During Endosperm Development in Maize Extensive study of starch deposition in wheat and maize has shown that the activity of ADP-glucose pyrophosphorylase is significantly altered in two starch mutants in corn (amylose extender and dull). In fact the expression of several enzyme activities are altered in thee mutants such that there are new ratios of several enzymes involved in the pathway of starch synthesis. FIGS. 7 and 8 show the considerable over-expression of several enzymes in the pathway of starch synthesis, particularly where there is a specific lesion in the normal pattern of starch deposition.

Of particular note is the finding that expression levels of ADP-glucose pyrophosphorylase are elevated up to 5-fold over the normal level of expression of this enzyme. This indicates that the ADP-glucose pyrophosphorylase promoter is responding to alterations in the flux of carbon to starch, but only when the flux is seriously disrupted as occurs with the full mutant genotype. This may be being brought about by some interaction with endosperm sucrose concentration which is very significantly elevated in the full mutant. These previously unknown findings show that, whilst the ADP-glucose pyrophosphorylase gene is responding similarly to that seen with some other enzymes in the pathway, this enzyme is the most responsive.

The above finding indicates that the promoter sequence for ADP-glucose pyrophosphorylase in maize is somehow more responsive. It therefore may be valuable as an endosperm-specific and responsive promoter for use in the genetic manipulation of core plants to alter their starch synthesising ability.

Using conventional techniques of molecular biology it is possible to use the cDNA clones for ADP-glucose pyrophosphorylase as a means of isolating and studying the genomic DNA sequence for this enzyme and hence isolate its promoter sequence. The nucleotide sequences provided are derived from the wheat enzyme(s) but there is assumed to be sufficient homology between wheat ADP-glucose pyrophosphorylase and other ADP-glucose pyrophosphorylase enzymes (such as the maize enzyme).

Once isolated, the effects of this promoter may be shown by fusing this sequence to a GUS "reporter-gene" and transforming the construct into plant cells. The transgenic plants may be used to study enzyme expression levels during various stresses that affect starch deposition.

Transgenic plants incorporating the ADP-glucose pyrophosphorylase gene promoter driving a donor gene encoding an enzyme involved in starch synthesis may also be produced.

Further studies of starch deposition in developing endosperm have involved the exposure of developing maize grain to a range of environmental temperatures for prolonged periods of time during grain filing. The effects of this on various enzyme activities involved in the pathway of starch synthesis was studied.

Figure 9:
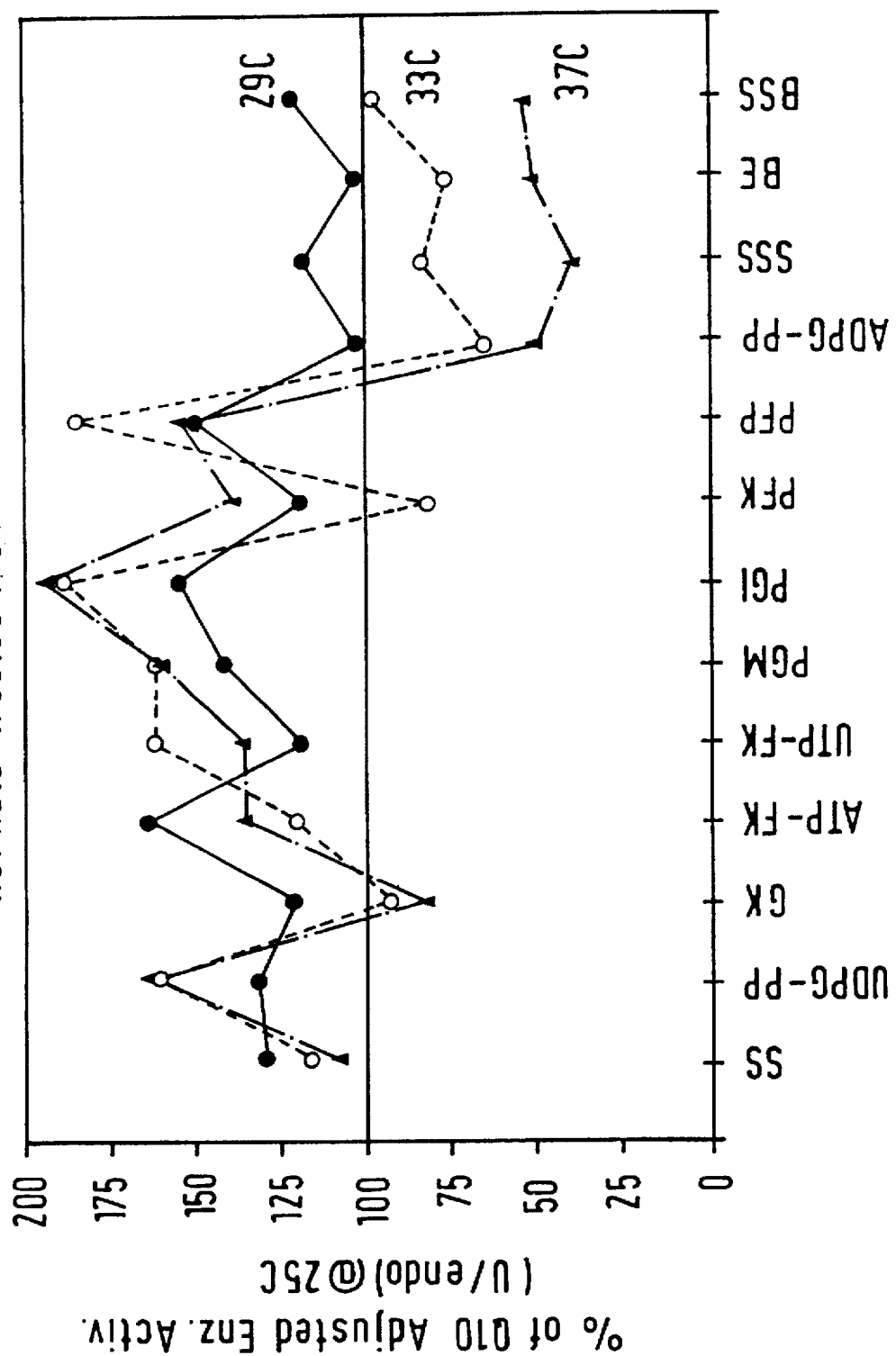
FIG. 9 shows the activity of starch synthetic enzymes at various temperatures.
Figure 10:
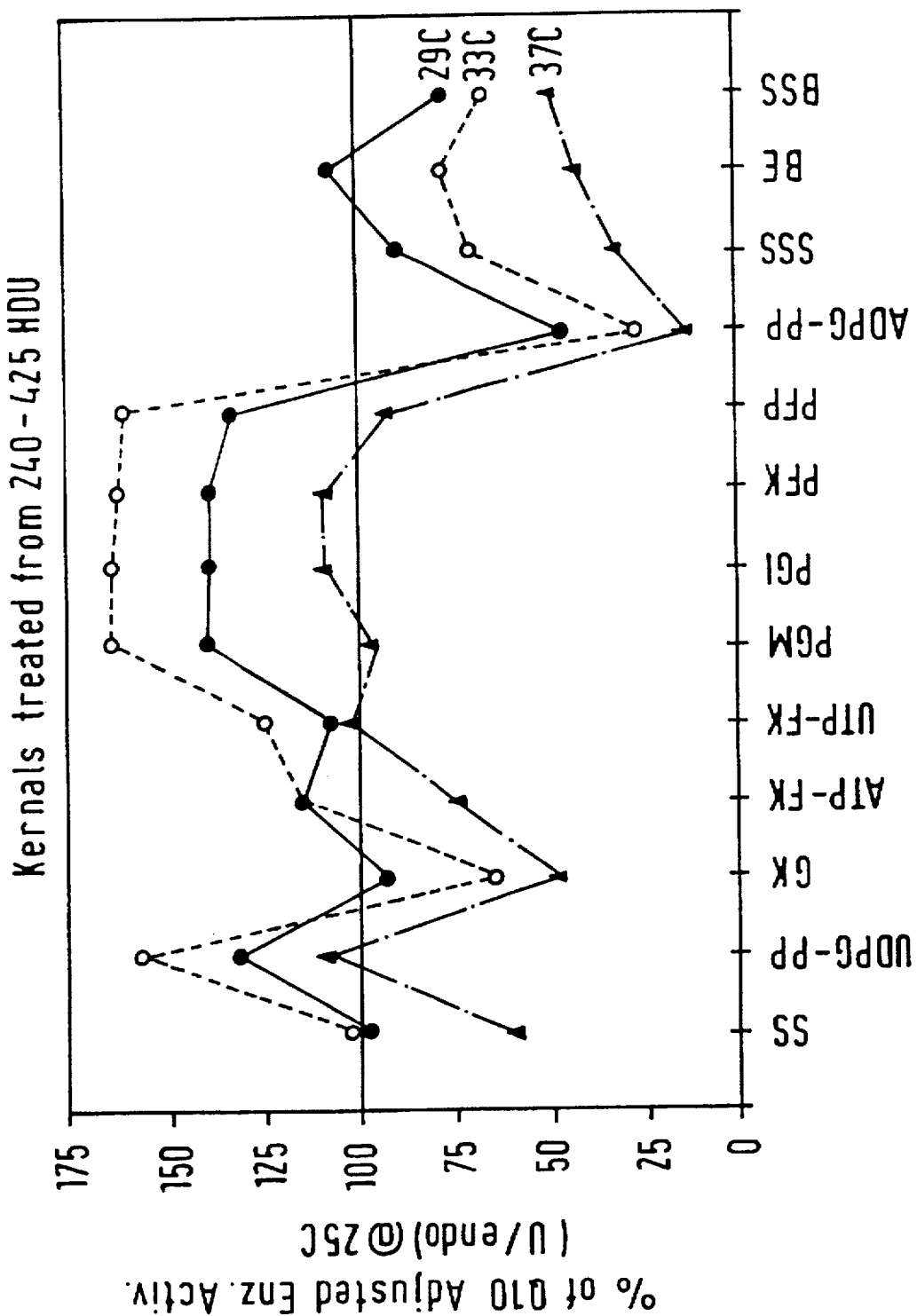
FIG. 10 shows the activity of starch synthetic enzymes at various temperatures.

FIGS. 9 and 10 show that for most of the enzymes in the pathway there was some moderate increase in activity after the accumulation of 185 heat units (HDU) due to the increased temperature. However, the amyloplast-located enzymes were distinctly different and were significantly lower in enzyme activity. ADP-glucose pyrophosphorylase in particular had the greatest decline in activity as a consequence of the elevated temperature. This change in enzyme levels during grain development at elevated temperatures is bringing-about a decreased duration of grain filling in cereal plants and may begin to explain how the duration of grain filling is being affected by increased temperature. The biochemical basis of this observation is not known at the present time, but plants may be screened for differences in the temperature-dependent duration of grain filling. Furthermore, by suing various probes to ADP-glucose pyrophosphorylase activity, protein, mRNAs etc., the mechanism(s) underlying this effect may be elucidated.

It may also be possible to reduce the temperature-dependence of these amyloplast enzymes by altering their molecular-sequence (amino-acid and/or nucleotide) or by changing their expression during development or by changing their amyloplast transit-peptide targeting sequences.

We claim:

1. A method of producing a plant with increased or decreased ability to synthesize starch comprising stably incorporating into the genome of a recipient plant at least one donor gene specifying an enzyme involved in the starch biosynthetic pathway such that the ability of the plant to produce starch is increased or decreased, wherein said donor gene has a nucleotide sequence as shown in FIG. 4, FIG. 5 or FIG. 6.

2. The method of claim 1, wherein said plant is selected from the group consisting of corn, wheat, rice, sorghum, barley, banana, apple, tomato, pear, cassava, potato, yam, turnip, rapeseed, sunflower, oil palm, coconut, linseed, groundnut, soya, bean and pea.

3. A method of producing a plant with increased or decreased ability to synthesize starch comprising stably incorporating into the genome of a recipient plant at least one donor gene specifying an enzyme involved in the starch biosynthetic pathway such that the ability of the plant to produce starch is increased or decreased, wherein said donor gene encodes an amino acid sequence as shown in FIG. 4, FIG. 5 or FIG. 6.

4. A plant having at least one donor gene, encoding an enzyme ADP-glucose pyrophosphorylase, stably incorporated into its genome such that its ability to produce starch is increased or decreased, wherein said donor gene encodes an amino acid sequence as shown in FIG. 4, FIG. 5 or FIG. 6.

5. The plant of claim 4, wherein said plant is selected from the group consisting of corn, wheat, rice, sorghum, barley, banana, apple, tomato, pear, cassava, potato, yam, turnip, rapeseed, sunflower, oil palm, coconut, linseed, groundnut, soya, bean and pea.

* * * * *